(12) United States Patent
Kurosawa et al.

(10) Patent No.: US 10,461,494 B2
(45) Date of Patent: Oct. 29, 2019

(54) LASER APPARATUS AND EXTREME ULTRAVIOLET LIGHT GENERATION SYSTEM

(71) Applicant: GIGAPHOTON INC., Tochigi (JP)

(72) Inventors: Yoshiaki Kurosawa, Oyama (JP); Takashi Suganuma, Oyama (JP)

(73) Assignee: GIGAPHOTON INC., Tochigi (JP)

( * ) Notice: Subject to any disclaimer, the term of this patent is extended or adjusted under 35 U.S.C. 154(b) by 0 days.

(21) Appl. No.: 16/055,656

(22) Filed: Aug. 6, 2018

(65) Prior Publication Data

US 2018/0351322 A1 Dec. 6, 2018

Related U.S. Application Data

(63) Continuation of application No. PCT/JP2016/058011, filed on Mar. 14, 2016.

(51) Int. Cl.
*H01S 3/134* (2006.01)
*H01S 3/036* (2006.01)
(Continued)

(52) U.S. Cl.
CPC ........... *H01S 3/134* (2013.01); *G01N 33/004* (2013.01); *G01N 33/0063* (2013.01);
(Continued)

(58) Field of Classification Search
CPC .......... H01S 3/134; H01S 3/005; H01S 3/034; H01S 3/036; H01S 3/1305; H01S 3/2316;
(Continued)

(56) References Cited

U.S. PATENT DOCUMENTS 9,425,576 B2 * 8/2016 Abe .................. H01S 3/134
2001/0050939 A1 12/2001 Ujazdowski et al.
(Continued)

FOREIGN PATENT DOCUMENTS

JP H02-142558 U 12/1990
JP H09-000405 U 7/1997
(Continued)

OTHER PUBLICATIONS

International Search Report issued in PCT/JP2016/058011; dated May 31, 2016.
(Continued)

*Primary Examiner* — Wyatt A Stoffa
(74) *Attorney, Agent, or Firm* — Studebaker & Brackett PC

(57) ABSTRACT

A laser apparatus according to one aspect of the present disclosure includes a master oscillator configured to output laser light, a plurality of amplifiers each configured to include carbon dioxide as a laser medium and amplify the laser light, a first optical path pipe configured to cover a laser optical path between the amplifiers, a gas supply port configured to supply, into the first optical path pipe, gas having lower carbon dioxide concentration than that of the air, a first carbon dioxide densitometer configured to measure carbon dioxide concentration in the first optical path pipe, and an alarm device configured to issue an alarm when the carbon dioxide concentration measured by the first carbon dioxide densitometer exceeds a preset prescribed value.

20 Claims, 9 Drawing Sheets

(51) Int. Cl.
*G01N 33/00* (2006.01)
*G03F 7/20* (2006.01)
*H01S 3/034* (2006.01)
*H01S 3/13* (2006.01)
*H01S 3/23* (2006.01)
*H01S 3/00* (2006.01)
*G01N 21/59* (2006.01)
*H01S 3/223* (2006.01)

(52) U.S. Cl.
CPC .......... *G03F 7/70033* (2013.01); *H01S 3/005* (2013.01); *H01S 3/034* (2013.01); *H01S 3/036* (2013.01); *H01S 3/1305* (2013.01); *H01S 3/2316* (2013.01); *G01N 21/5907* (2013.01); *H01S 3/0071* (2013.01); *H01S 3/1306* (2013.01); *H01S 3/2232* (2013.01)

(58) Field of Classification Search
CPC ... H01S 3/0071; H01S 3/1306; G01N 33/004; G01N 33/0063; G01N 21/5907; G03F 7/70033
See application file for complete search history.

(56) References Cited

U.S. PATENT DOCUMENTS

| | | |
|---|---|---|
| 2002/0006149 A1 | 1/2002 | Spangler et al. |
| 2002/0021728 A1 | 2/2002 | Newman et al. |
| 2002/0044586 A1* | 4/2002 | Myers .................. G01J 9/00 372/57 |
| 2002/0085606 A1 | 7/2002 | Ness et al. |
| 2002/0105994 A1 | 8/2002 | Partlo et al. |
| 2002/0105996 A1 | 8/2002 | Rokni et al. |
| 2002/0150138 A1 | 10/2002 | Pan et al. |
| 2002/0191654 A1 | 12/2002 | Klene et al. |
| 2003/0099269 A1 | 5/2003 | Ershov et al. |
| 2003/0118072 A1 | 6/2003 | Wittak et al. |
| 2004/0042521 A1* | 3/2004 | Ariga .................. H01S 3/10092 372/55 |
| 2011/0141865 A1* | 6/2011 | Senekerimyan ........ G01J 1/429 369/47.15 |
| 2013/0000773 A1* | 1/2013 | Jiang ...................... H01S 3/036 141/8 |
| 2014/0334514 A1* | 11/2014 | Tanino ................. B23K 26/064 372/55 |
| 2015/0334814 A1 | 11/2015 | Moriya et al. |
| 2016/0141823 A1 | 5/2016 | Nishio |

FOREIGN PATENT DOCUMENTS

| | | |
|---|---|---|
| JP | H11-008426 A | 1/1999 |
| JP | 2008-034871 A | 2/2008 |
| JP | 2008-253967 A | 10/2008 |
| JP | 2013-513929 A | 4/2013 |
| JP | 2013-165256 A | 8/2013 |
| JP | 2014-170885 A | 9/2014 |

OTHER PUBLICATIONS

The International Preliminary Report on Patentability (Chapter I) and Translation of Written Opinion of the International Searching Authority; PCT/JP2016/058011; dated Sep. 18, 2018.

* cited by examiner

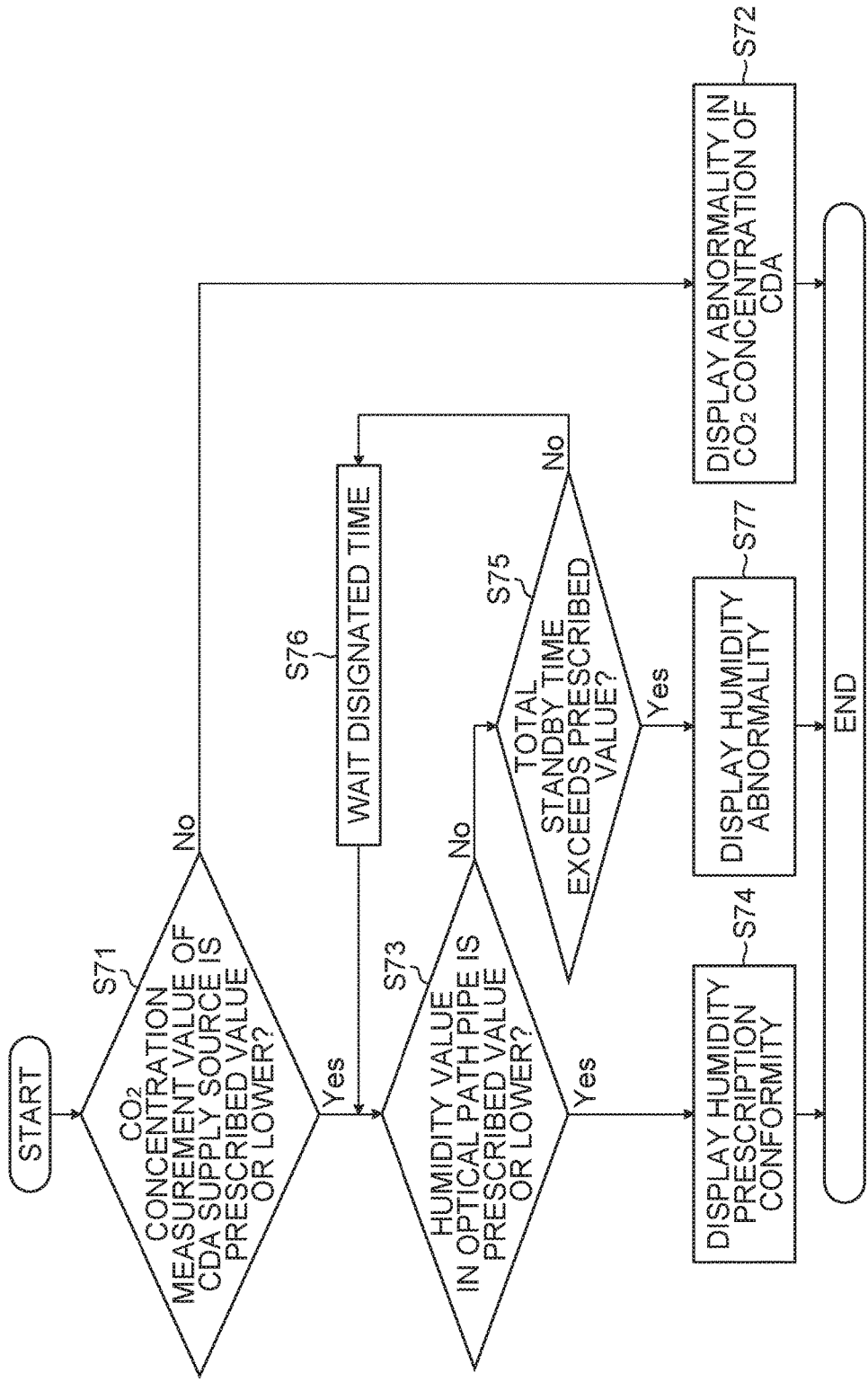

LASER APPARATUS AND EXTREME ULTRAVIOLET LIGHT GENERATION SYSTEM

CROSS-REFERENCE TO RELATED APPLICATIONS

The present application is a continuation application of International Application No. PCT/JP2016/058011 filed on Mar. 14, 2016. The content of the application is incorporated herein by reference in its entirety.

BACKGROUND

1. Technical Field

The present disclosure relates to a laser apparatus and an extreme ultraviolet light generation system.

2. Related Art

In recent years, along with microfabrication in the semiconductor manufacturing process, fine transfer patterns in photolithography of the semiconductor manufacturing process are developed rapidly. In the next generation, microfabrication of 20 nm or smaller will be required. Accordingly, it is desirable to develop an exposure device in which a device for generating extreme ultraviolet (EUV) light having a wavelength of about 13 nm and a reflection reduction projection optical system are combined.

As EUV light generation devices, three types of devices are proposed, namely, a laser produced plasma (LPP) type device that uses plasma generated when a target material is irradiated with laser light, a discharge produced plasma (DPP) type device that uses plasma generated by discharging, and a synchrotron radiation (SR) type device that uses orbital radiation light.

CITATION LIST

Patent Literature

Patent Literature 1: Japanese Patent Application Laid-Open No. 2013-165256
Patent Literature 2: Japanese Patent Application Laid-Open No. 2008-253967

SUMMARY

A laser apparatus according to one aspect of the present disclosure may include a master oscillator, a plurality of amplifiers, a first optical path pipe, a gas supply port, a first carbon dioxide densitometer, and an alarm device. The master oscillator may be configured to output laser light. Each of the amplifiers may be configured to include carbon dioxide as a laser medium and amplify the laser light. The first optical path pipe may be configured to cover a laser optical path between the amplifiers. The gas supply port may be configured to supply, into the first optical path pipe, gas having lower carbon dioxide concentration than that of the air. The first carbon dioxide densitometer may be configured to measure carbon dioxide concentration in the first optical path pipe. To the alarm device, a measurement result of the first carbon dioxide densitometer may be input. The alarm device may be configured to issue an alarm when the carbon dioxide concentration measured by the first carbon dioxide densitometer exceeds a preset prescribed value of carbon dioxide concentration.

A laser apparatus according to one aspect of the present disclosure may include a master oscillator, a plurality of amplifiers, a first optical path pipe, a gas supply port, a carbon dioxide densitometer, a first hygrometer, and an alarm device. The master oscillator may be configured to output laser light. Each of the amplifiers may be configured to include carbon dioxide as a laser medium and amplify the laser light. The first optical path pipe may be configured to cover a laser optical path between the amplifiers. The gas supply port may be configured to supply, into the first optical path pipe, gas having lower carbon dioxide concentration than that of the air. The carbon dioxide densitometer may be configured to measure carbon dioxide concentration of the gas supplied from the first gas supply port. The first hygrometer may be configured to measure humidity in the first optical path pipe. To the alarm device, a measurement result of the carbon dioxide densitometer and a measurement result of the first hygrometer may be input. The alarm device may be configured to issue an alarm in both cases where the carbon dioxide concentration measured by the carbon dioxide densitometer exceeds a preset prescribed value of carbon dioxide concentration, and where the humidity measured by the first hygrometer exceeds a preset prescribed value of humidity.

BRIEF DESCRIPTION OF THE DRAWINGS

Some embodiments of the present disclosure will be described below as just examples with reference to the accompanying drawings.

FIG. 9 is a flowchart illustrating an operation of a laser apparatus according to a seventh embodiment.

EMBODIMENTS

Contents

1. Overall description of extreme ultraviolet light generation system
   1.1     Configuration
   1.2     Operation
2. Terms
3. Overall configuration of laser optical path in laser apparatus
   3.1     Configuration
   3.2     Operation
4   Problem -continued 5. First embodiment
  5.1 Configuration
  5.2 Operation
  5.3 Effect
6. Second embodiment
  6.1 Configuration
  6.2 Operation
  6.3 Effect
7. Third embodiment
  7.1 Configuration
  7.2 Operation
  7.3 Effect
8. Fourth embodiment
  8.1 Configuration
  8.2 Operation
  8.3 Effect
9. Fifth embodiment
  9.1 Configuration
  9.2 Operation
  9.3 Effect
10. Sixth embodiment
  10.1 Configuration
  10.2 Operation
  10.3 Effect
11. Seventh embodiment
  11.1 Configuration
  11.2 Operation
  11.3 Effect Hereinafter, embodiments of the present disclosure will be described in detail with reference to the drawings.

The embodiments described below illustrate some examples of the present disclosure, and do not limit the contents of the present disclosure. All of the configurations and the operations described in the embodiments are not always indispensable as configurations and operations of the present disclosure. The same constituent elements are denoted by the same reference signs, and overlapping description is omitted.

Figure 1:
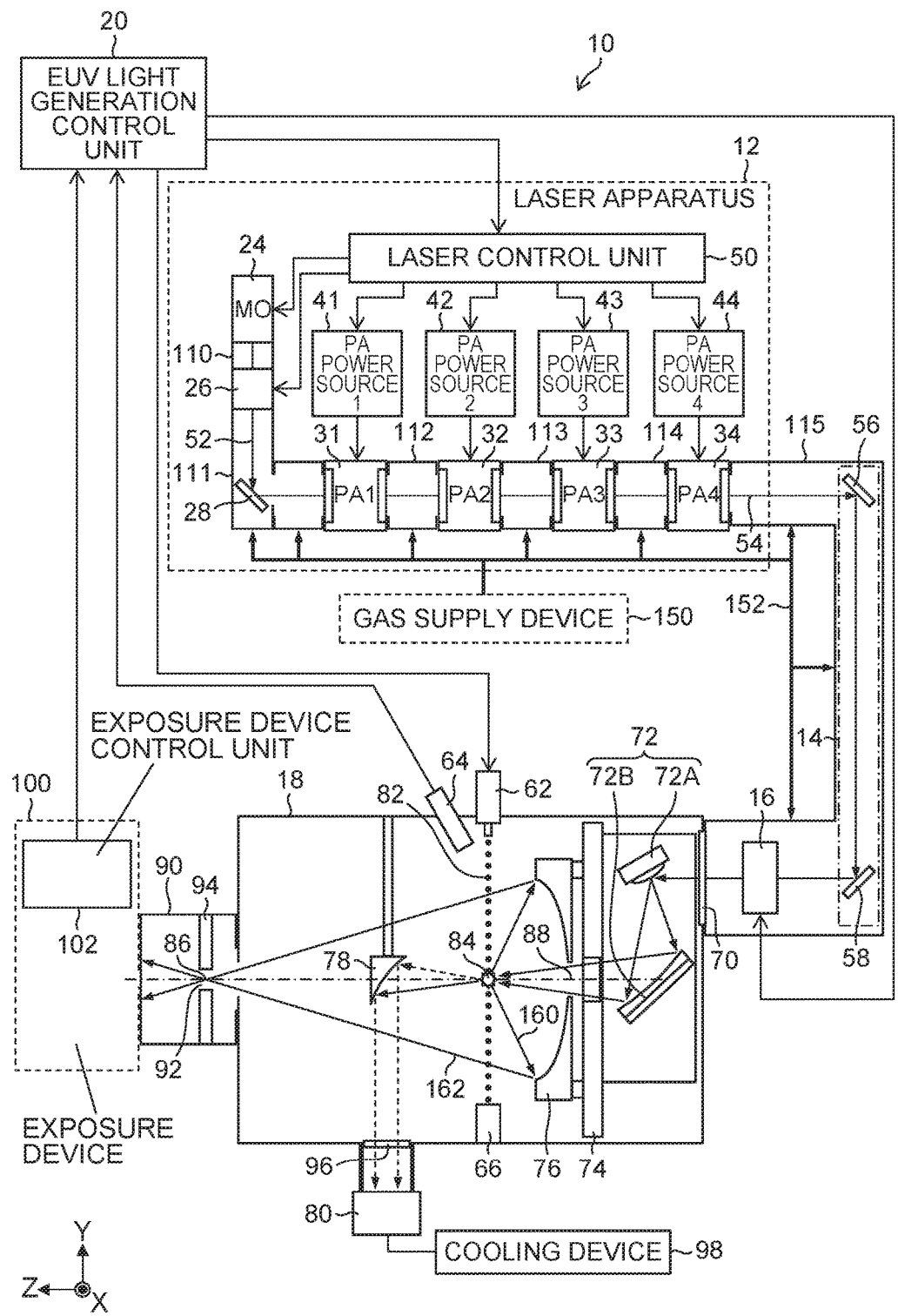
FIG. 1 is a diagram schematically illustrating a configuration of an exemplary LPP type EUV light generation system.

1. Overall Description of Extreme Ultraviolet Light Generation System 1.1 Configuration FIG. 1 schematically illustrates a configuration of an exemplary LPP type EUV light generation system 10. An EUV light generation system 10 includes a laser apparatus 12, a laser light transmission device 14, a beam regulator 16, a chamber 18, and an EUV light generation control unit 20.

The laser apparatus 12 includes a master oscillator 24, an optical isolator 26, a plurality of amplifiers 31-34, a plurality of amplifier power sources 41-44, and a laser control unit 50. The expression of amplifiers 31-34 means "amplifiers 31, 32, 33, 34". The expression of amplifier power sources 41-44 means "amplifier power sources 41, 42, 43, 44".

The laser apparatus 12 may further include optical components not illustrated, besides a first high reflective mirror 28, on the laser optical path. The first high reflective mirror 28 and the other optical components disposed on the laser optical path are configured to transmit and/or format laser light.

A combination of the master oscillator 24 and the amplifiers 31-34 constitute a master oscillator power amplifier (MOPA) system. The master oscillator 24 may output laser light including a wavelength of an amplification region of a $CO_2$ laser amplifier, with a given repetition frequency. The wavelength of pulse laser light 52, output from the master oscillator 24, is 10.59 μm, for example, and the given repetition frequency is 100 kHz, for example. As the master oscillator 24, a solid-state laser is adoptable. In FIG. 1, the master oscillator 24 is described as "MO".

The optical isolator 26 transmits and cuts off laser light according to an instruction from the laser control unit 50. Transmission of laser light by the optical isolator 26 may be referred to as "open" and cutoff may be referred to as "close". The optical isolator 26 is disposed on the laser optical path between the master oscillator 24 and the first-stage amplifier 31.

The first high reflective mirror 28 is disposed on the laser optical path between the optical isolator 26 and the first-stage amplifier 31. The first high reflective mirror 28 reflects the laser light output from the master oscillator 24 to make the laser light incident on the first-stage amplifier 31.

The respective amplifiers 31-34 are disposed on the optical path of the laser light output from the master oscillator 24 via the optical isolator 26 and the first high reflective mirror 28. In FIG. 1, the amplifiers 31-34 sequentially disposed on the optical path of the laser light are described such that, from the upstream side of the optical path, the first-stage amplifier 31 is "PA1", the second-stage amplifier 32 is "PA 2", the third-stage amplifier 33 is "PA3", and the fourth-stage amplifier 34 is "PA4". The upstream side of the optical path means a side closer to the master oscillator 24 on the optical path of the laser light. The laser light travels from the upstream side to the downstream side on the optical path.

While four amplifiers 31-34 are illustrated in FIG. 1, the number of amplifiers included in the MOPA system is not limited to this example. The laser apparatus 12 may have a configuration including "n" pieces of amplifiers. "n" may be an integer of 2 or larger. Each of the amplifiers 31-34 is a $CO_2$ laser amplifier using $CO_2$ laser gas as a medium. $CO_2$ laser gas is an example of a laser medium containing carbon dioxide.

The respective amplifiers 31-34 are connected with the corresponding amplifier power sources 41-44. In FIG. 1, it is described that the amplifier power source 41 connected with the amplifier 31 is a "PA power source 1", the amplifier power source 42 connected with the amplifier 32 is a "PA power source 2", the amplifier power source 43 connected with the amplifier 33 is a "PA power source 3", and the amplifier power source 44 connected with the amplifier 34 is a "PA power source 4".

The respective amplifier power sources 41-44 are connected with the laser control unit 50. The laser control unit 50 is connected with the EUV light generation control unit 20.

The laser light transmission device 14 includes an optical component for defining a travel direction of the laser light, and an actuator for regulating the position, posture, and the like of the optical component. As an exemplary optical component for defining the travel direction of the laser light, FIG. 1 illustrates the laser light transmission device 14 having a configuration including a second high reflective mirror 56 and a third high reflective mirror 58.

The beam regulator 16 is disposed on the laser optical path from the laser light transmission device 14 to a laser light condensing optical system 72. The beam regulator 16 regulates the divergence angle of laser light according to an instruction from the laser control unit 50. The beam regulator 16 may be included in the constituent elements of the laser apparatus 12.

The chamber 18 includes a target feeder 62, a target sensor 64, a target recovery device 66, a window 70, the laser light condensing optical system 72, a mirror holding member 74, an EUV light condensing mirror 76, a dumper mirror 78, and a beam dump device 80.

The chamber 18 is a sealable container. The chamber 18 may be formed in a hollow spherical shape or a hollow cylindrical shape, for example. The target feeder 62 feeds a target substance to the inside of the chamber 18, and is mounted so as to penetrate a wall of the chamber 18, for example.

The material of the target substance may include, but not limited to, tin, terbium, gadolinium, lithium, xenon, or a combination of any two or more of them. The target feeder 62 may output a target 82 made of the target substance toward a plasma generation region 84 in the chamber 18.

The target sensor 64 detects any of or a plurality of the presence, the trajectory, the position, and the velocity of the target 82. The target sensor 64 may have an imaging function.

The target recovery device 66 is disposed on an extended line in a direction in which the target 82 output from the target feeder 62 into the chamber 18 travels.

A wall of the chamber 18 has at least one through hole. The through hole is closed with a window 70. Pulse laser light 54 output from the laser apparatus 12 penetrates the window 70.

The inside of the chamber 18 is provided with the laser light condensing optical system 72, the mirror holding member 74, the EUV light condensing mirror 76, and the dumper mirror 78.

The laser light condensing optical system 72 condenses the laser light, made incident on the chamber 18, in the plasma generation region. The laser light condensing optical system 72 includes a convex mirror 72A and a laser light condensing mirror 72B, for example. The convex mirror 72A expands the beam cross-sectional area of the incident laser light to reflect the laser light to the laser light condensing mirror. The convex mirror 72A may be an elliptical mirror. The laser light condensing mirror 72B may be an off-axis paraboloid mirror.

The mirror holding member 74 is a member fixed to the chamber 18, and holding the laser light condensing optical system 72 and the EUV light condensing mirror 76. The EUV light condensing mirror 76 may be held via an appropriate holder.

The EUV light condensing mirror 76 includes a spheroidal reflection surface, and has a first focus and a second focus, for example. On the surface of the EUV light condensing mirror 76, a multilayer reflection film in which molybdenum and silicon are alternately layered is formed, for example.

The EUV light condensing mirror 76 is disposed such that the first focus thereof is positioned in the plasma generation region 84 and the second focus thereof is positioned at an intermediate focusing point (IF) 86, for example. A center portion of the EUV light condensing mirror 76 is provided with a through hole 88 through which pulse laser light 54 passes.

The EUV light generation system 10 also includes a connecting section 90 that allows the inside of the chamber 18 and the inside of an exposure device 100 to communicate with each other. The inside of the connecting section 90 is provided with a wall 94 having an aperture 92. The wall 94 may be disposed such that the aperture 92 is positioned at the second focus position of the EUV light condensing mirror 76.

The dumper mirror 78 is disposed on the laser optical path downstream of the plasma generation region 84 in the laser light travel direction, and reflects the laser light passing through the plasma generation region 84 toward the beam dump device 80. The dumper mirror 78 may reflect the incident laser light to make it to be parallel light, or may be an off-axis paraboloid mirror. The dumper mirror 78 may have a heater, not illustrated, that heats the reflection surface thereof to be a temperature of a melting point of the target substance or higher.

The beam dump device 80 is disposed at a position where the laser light reflected by the dumper mirror 78 is made incident. The laser light reflected by the dumper mirror 78 is made incident on the beam dump device 80 via a dumper window 96 disposed on the chamber wall. The beam dump device 80 is connected with a cooling device 98. The cooling device 98 lowers the temperature of a cooling medium flowing through the inside of the beam dump device 80. The cooling medium circulates between the beam dump device 80 and the cooling device 98.

The exposure device 100 includes an exposure device control unit 102 which is connected with the EUV light generation control unit 20.

The laser optical path from the master oscillator 24 to the window 70 of the chamber 18 in the laser apparatus 12 is covered with optical path pipes 110-115. The expression of optical path pipes 110-115 means "optical path pipes 110, 111, 112, 113, 114, 115". Part or whole of the optical path pipes 110-115 are linked with a pipe 152 connected to a gas supply device 150. The gas supply device 150 may be a CDA supply device, for example. CDA is an abbreviation of clean dry air. CDA corresponds to a form of "gas having lower carbon dioxide concentration than that of the air". The gas supply device 150 is only necessary to supply gas having lower carbon dioxide concentration than that of the air. The gas supply device 150 is not limited to a CDA supply device. It may be a device that supplies nitrogen gas.

In the present disclosure, control units such as the EUV light generation control unit 20, the laser control unit 50, and the exposure device control unit 102 can be realized by a combination of hardware and software of one or a plurality of computers. Software has the same meaning as a program. It is also possible to realize functions of a plurality of control units by one control device. Further, in the present disclosure, the EUV light generation control unit 20, the laser control unit 50, the exposure device control unit 102, and the like may be connected with each other over a communication network such as a local area network or the Internet. In a distributed computing environment, a program module may be stored in memory storage devices of both local and remote.

1.2 Operation

Operation of the exemplary LPP type EUV light generation system 10 will be described with reference to FIG. 1. In the case where the EUV light generation system 10 outputs EUV light, an EUV light output instruction is transmitted from the exposure device control unit 102 of the exposure device 100 to the EUV light generation control unit 20. The EUV light generation control unit 20 outputs the target 82 to the target feeder 62, based on the EUV output instruction from the exposure device 100.

The EUV light generation control unit 20 transmits, to the target feeder 62, a target output signal to instruct outputting of the target 82. The target feeder 62 outputs the target 82 made of a target substance into the chamber 18, in accordance with the target output signal. The target 82 is a droplet of a molten target substance, for example.

The target sensor 64 detects the target 82, and outputs a target detection signal to the EUV light generation control unit 20. The target detection signal may be a passage timing signal indicating the timing when the target 82 passes through a given position.

The EUV light generation control unit 20 outputs, to the laser control unit 50 of the laser apparatus 12, a light emission trigger generated by adding a given delay time to the target detection signal. When the light emission trigger is input, the laser control unit 50 outputs a laser output signal to the master oscillator 24.

The laser control unit 50 also turns on the amplifier power sources 41-44 prior to the output of the laser output signal. Thereby, the respective amplifier power sources 41-44 supply voltage or electric current to the inner electrodes of the respective amplifiers 31-34 to thereby allow the respective amplifiers 31-34 to be in a state capable of performing amplification.

The master oscillator 24 outputs laser light in synchronization with the laser output signal. The laser control unit 50 opens the optical isolator 26 in synchronization with the output of the laser light by the master oscillator 24. The laser light, passing through the optical isolator 26, is reflected by the first high reflective mirror 28 and is made incident on the first-stage amplifier 31. The first-stage amplifier 31 amplifies the laser light output from the master oscillator 24 and outputs it. The laser light output from the amplifier 31 is made incident on the second-stage amplifier 32. The second-stage amplifier 32 amplifies the laser light output from the first-stage amplifier 31. Similarly, the laser light is amplified sequentially, and the pulse laser light 54 amplified and output by the fourth-stage amplifier 34, that is in the final stage, is made incident on the laser light transmission device 14.

As described above, the laser light output from the master oscillator 24 is amplified by the amplifiers 31-34, and is made incident on the beam regulator 16 via the laser light transmission device 14. The beam regulator 16 regulates the divergence angle of the incident laser light to output the light. The laser light output from the beam regulator 16 passes through the window 70, and then, is input to the chamber 18. The power of the laser light output from the laser apparatus 12 reaches several kW to several tens kW.

The laser light made incident on the chamber 18 is condensed by the laser light condensing optical system 72, and is radiated to the target 82 that reached the plasma generation region. The target 82 is irradiated with at least one pulse included in the pulse laser light 54. Thereby, EUV light can be obtained. This means that the target 82 irradiated with the pulse laser light is made into plasma, and radiation light 160 is emitted from the plasma. EUV light 162 included in the radiation light 160 is selectively reflected by the EUV light condensing mirror 76. The EUV light 162 reflected by the EUV light condensing mirror 76 is condensed at the intermediate focusing point 86 and is output to the exposure device 100.

The irradiation diameter of the laser light, when the laser light is condensed and radiated to the target 82, may be larger than the diameter of the target 82. Part of the laser light may not be radiated to the target 82 and may be made incident on the dumper mirror 78.

The laser light reflected by the dumper mirror 78 is absorbed by the beam dump device 80 via the dumper window 96, and is converted to heat. The heat generated at this time is discharged to the outside by a cooling device 98.

There is a case that laser light is not radiated to the target 82. For example, while laser light is kept output for stabilizing output of the laser apparatus 12 or regulating the optical path, there is a case of avoiding irradiation intentionally by stopping feeding of the target 82 or changing the delay time. In such a case, laser light is not radiated to the target 82, and is made incident on the dumper mirror 78 while maintaining the laser output.

The target recovery device 66 recovers the target 82 not irradiated with the laser light and passing through the plasma generation region 84, or part of a droplet not distributed even with irradiation of the laser light.

The EUV light generation control unit 20 presides over the control of the entire EUV light generation system 10. The EUV light generation control unit 20 processes a detection result of the target sensor 64. The EUV light generation control unit 20 may control the output timing of the target 82, the output direction of the target 82, and the like, for example, based on the detection result of the target sensor 64. Furthermore, the EUV light generation control unit 20 may control the oscillation timing of the laser apparatus 12, the travel direction of the pulse laser light 54, and the condensing position of the pulse laser light 54, and the like, for example. The aforementioned various types of control are mere examples. Other types of control may be added as required, or part of the control functions may be omitted.

In FIG. 1, a direction of deriving the EUV light 162 from the chamber 18 toward the exposure device 100 is assumed to be a Z axis. An X axis and a Y axis are assumed to be axes orthogonal to the Z axis and orthogonal to each other. The dripping direction of the target 82 is assumed to be a direction parallel to the Y axis.

2. Terms

"Target" is an object to be irradiated with laser light introduced to the chamber. The target irradiated with laser light is made into plasma and emits EUV light. A droplet made of a liquid target substance is a form of a target.

"Plasma light" is radiation light emitted from a target made into plasma. The radiation light includes EUV light.

The expression "EUV light" is an abbreviation of "extreme ultraviolet light".

"$CO_2$" means carbon dioxide.

A term "optical component" has the same meaning as an optical element or an optical member.

3. Overall Configuration of Laser Optical Path in Laser Apparatus 12

3.1 Configuration

Figure 2:
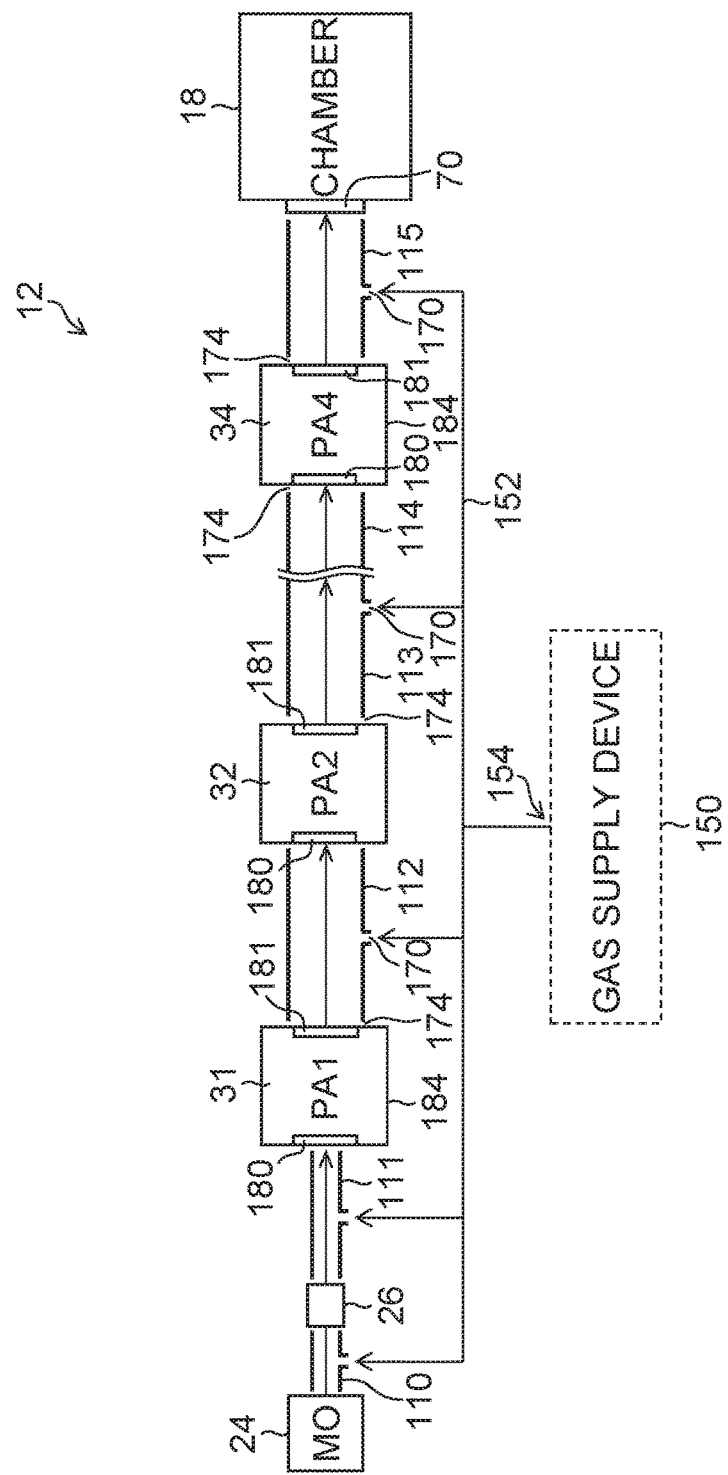
FIG. 2 is a schematic diagram illustrating a schematic configuration of a laser apparatus.

FIG. 2 is a schematic diagram illustrating the laser optical path part in the laser apparatus 12. The laser optical path from the master oscillator 24 to the chamber 18 is almost entirely covered with the optical path pipes 110-115. The optical path pipes 110-115 may cover the optical isolator 26, the first high reflective mirror 28, the second high reflective mirror 56, the third high reflective mirror 58, and other optical components. For example, in FIG. 2, the optical path pipe 110 and the optical path pipe 111 may be integrally connected with each other, and the integrated optical path pipe may cover the optical isolator 26.

Each of the optical path pipes 110-115 is provided with a gas flow inlet 170. The gas flow inlet 170 is connected with a pipe 152 linked with the gas supply device 150. It is preferable that the gas flow inlet 170 is disposed near the center in the longitudinal direction of each of the optical path pipes 110-115.

The pipe 152 makes the gas, introduced from a gas introduction part 154, branched by a manifold to thereby guide the gas to the gas flow inlet 170 of each of the optical path pipes 110-115. The gas introduction part 154 of the pipe 152 is connected with the gas supply device 150. The pipe 152 is provided with a flow rate adjustment valve not illustrated. The gas flow rate to each of the optical path pipes 110-115 is adjusted by the flow rate adjustment valve.

Each of the optical path pipes 110-115 has a discharge hole 174 communicating with the outside. The discharge hole 174 may be formed of a gap in the connecting section between each of the optical path pipes 110-115 and each of the amplifiers 31-34, the chamber 18, or the like. The discharge hole 174 is not necessarily provided to every optical path pipe.

In the connecting section between each of the optical path pipes 110-115 and each of the amplifiers 31-34, the chamber 18, or the like, one end or both ends of the optical path pipe is closed with a window. Each of the amplifiers 31-34 has an incident side window 180 on which laser device is made incident, and an emission side window 181 from which amplified laser light is emitted, and is covered with a laser cover 184.

At both ends of each of the optical path pipes 112-114 disposed between the respective amplifiers 31-34 is provided with the incident side window 180 or the emission side window 181. At one end of both ends of the optical path pipe 110, an emission side window, not illustrated, of the master oscillator 24 is disposed, and the optical isolator 26 is disposed at the other end. The optical isolator 26 functions as a window closing one end of the optical path pipe 110. At one end of both ends of the optical path pipe 111, the optical isolator 26 is disposed, and the incident side window 180 of the amplifier 31 is disposed at the other end. The optical isolator 26 functions as a window closing one end of each of the optical path pipe 110 and the optical path pipe 111.

At one end of both ends of the optical path pipe 115 disposed between the amplifier 34 and the chamber 18, the emission side window 181 of the amplifier 34 is disposed, and the window 70 of the chamber 18 is disposed at the other end. While FIG. 2 illustrates a configuration in which both ends of all of the optical path pipes 110-115 are closed with windows, in some optical path pipes, some ends thereof may not be closed with windows.

3.2 Operation

The gas supply device 150 supplies CDA to the insides of the optical path pipes 110-115. CDA is dry air in which the dew-point temperature thereof is managed to be −70° C. or lower. The gas supply device 150 generates CDA managed to be in a given humidity range, and supplies CDA to the respective optical path pipes 110-115 via the pipe 152. The CDA flows through the laser optical path covered with the optical path pipes 110-115, and is discharged from the discharge hole 174 to the outside.

When the clean CDA in which the humidity is managed flows through the laser optical path, deterioration due to dew condensation and moisture adsorption of the optical components arranged on the laser optical path is suppressed. Such an action by the gas flow is referred to as "purge".

The gas pressure supplied from the gas supply device 150 to each of the optical path pipes 110-115 is set to a pressure sufficiently higher than the atmospheric pressure. By setting the pressure in each optical path pipe to be a value higher than the atmospheric pressure, it is possible to suppress inflow of the air from the outside to the inside of the optical path pipe.

4. Problem

There is a case where $CO_2$ is contaminated in the CDA supplied from the gas supply device 150 to the laser optical path. As $CO_2$ in the CDA absorbs laser light, the gas on the laser optical path is heated and the temperature thereof rises. Due to a temperature rise of the gas on the laser optical path, refractive index distribution occurs in the laser optical path, causing a heat lens effect.

By the heat lens effect, the laser light may be in an unintentional divergent state. As such, the laser light may not reach the chamber 18 with a given energy density, whereby the EUV energy may be lowered. Moreover, by the heat lens effect, the laser light may be in an unexpected condensed state on a surface of an optical component in the optical path, whereby the optical component may be broken.

5. First Embodiment 5.1 Configuration

Figure 3:
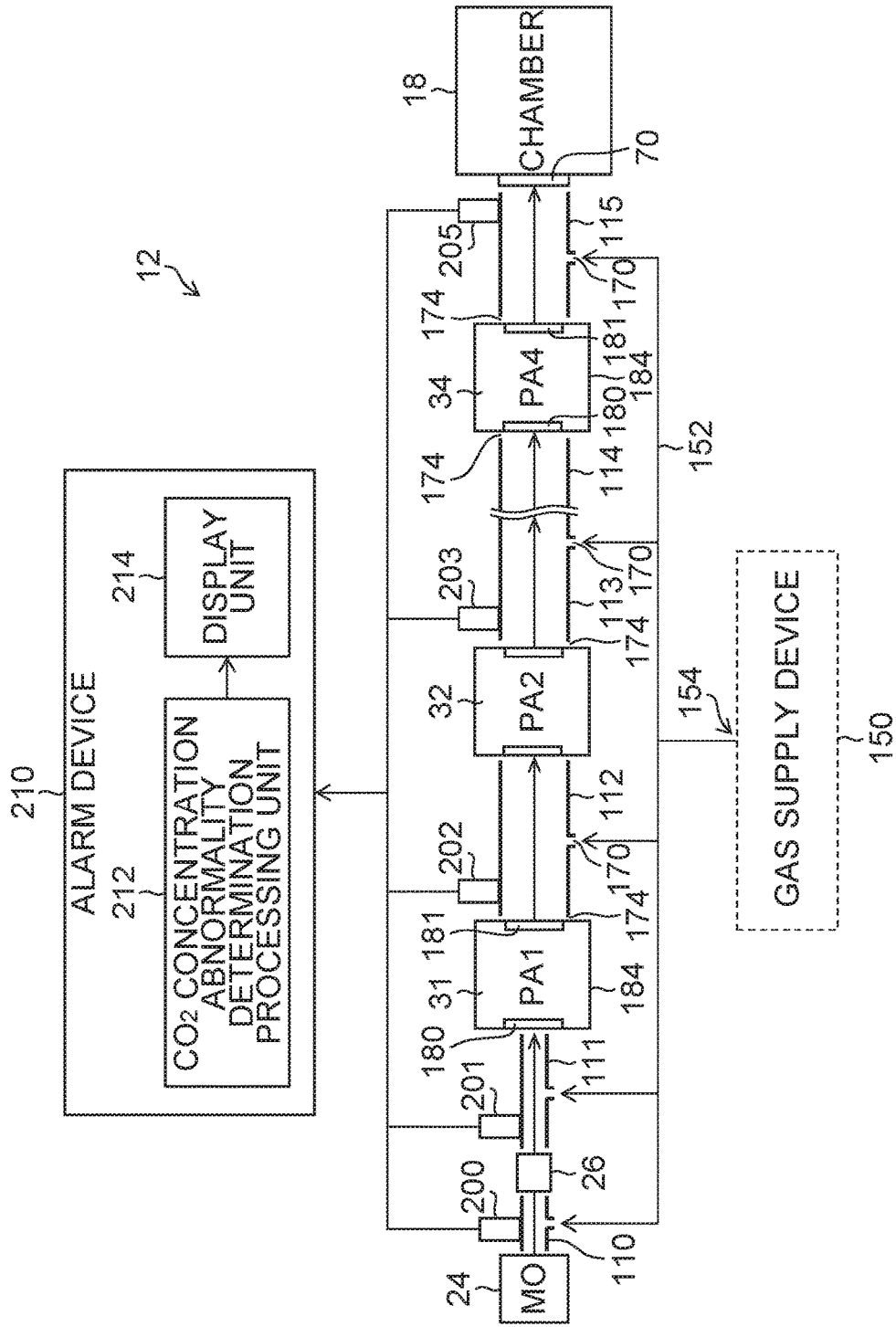
FIG. 3 is a schematic diagram illustrating a configuration of a laser apparatus according to a first embodiment.

FIG. 3 is a schematic diagram illustrating a configuration of a laser apparatus 12 according to a first embodiment. Different points from FIG. 2 will be described with use of FIG. 3.

As illustrated in FIG. 3, the laser apparatus 12 according to the first embodiment includes $CO_2$ densitometers 200-205 on the optical path pipes 110-115 covering the laser optical path. The expression of $CO_2$ densitometers 200-205 means "$CO_2$ densitometers 200, 201, 202, 203, 205 and a $CO_2$ densitometer, not illustrated, provided to the optical path pipe 114". In FIG. 3, illustration of the $CO_2$ densitometer provided to the optical path pipe 114 is omitted. The $CO_2$ densitometer provided to the optical path pipe 114 may be denoted by a reference numeral 204 in some cases.

A $CO_2$ densitometer may be provided to each of the entire optical path pipes 110-115, or may be provided to some optical path pipes. A $CO_2$ densitometer may be provided to each optical path pipe in which laser light having a given power density or higher propagates, among the optical path pipes 110-115. The given power density may be 1.2 $kW/cm^2$, for example. It is preferable that a plurality of $CO_2$ densitometers are disposed in the laser apparatus 12. It is also possible to dispose a plurality of $CO_2$ densitometers on one optical path pipe.

In the case of the laser apparatus 12 in which amplification is performed in stages by a plurality of amplifiers 31-34, the power density is higher in latter stages of amplification. Accordingly, it is preferable to have a configuration in which a $CO_2$ densitometer is disposed in an optical path pipe covering a laser optical path between amplifiers in the amplification latter-stage side including at least the final-stage amplifier 34. In the case of FIG. 3, it is preferable to provide $CO_2$ densitometers to at least the optical path pipes 114 and 115.

In general, in a laser apparatus in which N pieces of $CO_2$ laser amplifiers are used to perform amplification in N stages, it is preferable to have a configuration in which a $CO_2$ densitometer is disposed in an optical path pipe covering a laser optical path between amplifiers on the amplification latter-stage side including at least a final-stage amplifier, among the laser optical paths between the N pieces of amplifies. N may be an integer of 3 or larger. For example, in the case of using eight amplifiers, it is possible to provide a $CO_2$ densitometer in an optical path pipe covering a laser optical path between amplifiers of the fourth stage and after, respectively.

As the $CO_2$ densitometers 200-205, $CO_2$ densitometers of non-dispersive infrared absorption type may be used. Each of the $CO_2$ densitometers 200-205 measures $CO_2$ concentration in each of the optical path pipes 110-115 where it is provided. $CO_2$ concentration in an optical path pipe means $CO_2$ concentration of the gas in the optical path pipe. Gas in an optical path pipe may include a component of the air contaminated in the optical path pipe from the outside, in addition to the CDA supplied into the optical path pipe. This means that the $CO_2$ densitometers 200-205 each measure the $CO_2$ concentration of the gas on the laser optical path.

The laser apparatus 12 also includes an alarm device 210 connected with the $CO_2$ densitometers 200-205. A laser controller that functions as the laser control unit 50 described in FIG. 1 may also function as the alarm device 210. The alarm device 210 includes a $CO_2$ concentration abnormality determination processing unit 212 and a display unit 214. The $CO_2$ concentration abnormality determination processing unit 212 performs processing to determine presence or absence of abnormality in $CO_2$ concentration, based on a measurement result of the $CO_2$ concentration obtained, for example, from the $CO_2$ densitometer 202.

To the alarm device 210, a $CO_2$ concentration prescribed value is input, and information of the $CO_2$ concentration prescribed value is stored therein. The $CO_2$ concentration prescribed value is a value of $CO_2$ concentration prescribing the allowable upper limit of $CO_2$ concentration in the laser optical path, for example. The $CO_2$ concentration prescribed value is used as a determination basis in the case of determining whether the $CO_2$ concentration in the laser optical path is normal or abnormal. The $CO_2$ concentration prescribed value corresponds to a threshold of the $CO_2$ concentration. The $CO_2$ concentration prescribed value corresponds to one form of a "prescribed value of carbon dioxide concentration". The $CO_2$ concentration prescribed value may be set in advance in the alarm device 210, or input from a user interface not illustrated.

As the $CO_2$ concentration prescribed value, a uniform value may be set for all of the $CO_2$ densitometers 200-205 provided to the laser optical path. For example, all of the $CO_2$ densitometers 200-205 may be set uniformly to 50 ppm or lower.

Alternatively, the $CO_2$ concentration prescribed value may be set according to at least one of the power density of the laser light at the position of an optical path pipe, and a laser light propagation distance in the optical path pipe. Different values may be set to the respective $CO_2$ densitometers 200-205.

For example, the $CO_2$ concentration prescribed value of a $CO_2$ densitometer disposed on an optical path pipe of an optical path having low power density may be higher than 50 ppm. Meanwhile, the $CO_2$ concentration prescribed value of a $CO_2$ densitometer disposed on an optical path pipe of an optical path having a short laser light propagation distance may be higher than 50 ppm.

Assuming that the master oscillator 24 side is an upstream side and the chamber 18 side is a downstream side in a laser optical path, a $CO_2$ concentration prescribed value of a $CO_2$ densitometer disposed on the upstream side may be set higher than a $CO_2$ concentration prescribed value of a $CO_2$ densitometer disposed on the downstream side. This means that different $CO_2$ concentration prescribed values may be set to at least two $CO_2$ densitometers disposed at different positions, among a plurality of $CO_2$ densitometers.

The display unit 214 displays information informing abnormality in the $CO_2$ concentration in the laser optical path, based on a determination result of the $CO_2$ concentration abnormality determination processing unit 212. As the display unit 214, a display device such as a liquid crystal display may be adopted. Further, the alarm device 210 may include a configuration that outputs warning light, warning sound, or an alarm by a sound output.

Each of the optical path pipes 112-114 disposed between the amplifiers 31-34 corresponds to a form of a "first optical pipe". Each of the $CO_2$ densitometer 202 that measures the $CO_2$ concentration in the optical path pipe 112, the $CO_2$ densitometer 203 that measures the $CO_2$ concentration in the optical path pipe 113, and a $CO_2$ densitometer, not illustrated, that measures the $CO_2$ concentration in the optical path pipe 114, corresponds to a form of a "first carbon dioxide densitometer". Each of the optical path pipes 110 and 111 corresponds to a form of a "second optical pipe". Each of the $CO_2$ densitometer 200 that measures the $CO_2$ concentration in the optical path pipe 110 and the $CO_2$ densitometer 201 that measures the $CO_2$ concentration in the optical path pipe 111 corresponds to a form of a "second carbon dioxide densitometer".

The optical path pipe 115 disposed between the amplifier 34 and the chamber 18 corresponds to a form of a "third optical pipe". The $CO_2$ densitometer 205 that measures the $CO_2$ concentration in the optical path pipe 115 corresponds to a form of a "third carbon dioxide densitometer". The gas introduction part 154 of the pipe 152 connected with the gas supply device 150 corresponds to a form of a "gas supply port". Further, the gas flow inlet 170 of each optical path pipe corresponds to a form of a "gas supply port".

5.2 Operation

To the alarm device 210, measurement results of the respective $CO_2$ densitometers 202-205 are input. The alarm device 210 monitors the $CO_2$ concentration in the optical path pipes based on measurement signals from the $CO_2$ densitometers 202-205, and issues an alarm when the concentration exceeds prescribed $CO_2$ concentration. The prescribed $CO_2$ concentration means a preset $CO_2$ concentration prescribed value. When $CO_2$ concentration exceeding the prescribed $CO_2$ concentration is detected, the alarm device 210 outputs, to the display unit 214, information informing that the $CO_2$ concentration in the laser optical path is abnormal.

In addition to the alarm outputting function, the alarm device 210 may determine propriety of laser oscillation. When the alarm device 210 issues an alarm indicating abnormality in $CO_2$ concentration, laser oscillation is not allowed. According to the determination of abnormality in $CO_2$ concentration, the alarm device 210 may transmit a signal controlling propriety of laser oscillation to the laser control unit 50.

When the laser control unit 50 receives a signal of "laser oscillation allowed" from the alarm device 210, the laser control unit 50 outputs a laser output signal. Meanwhile, when then the laser control unit 50 receives a signal of "laser oscillation not allowed" from the alarm device 210, the laser control unit 50 does not output a laser output signal.

5.3 Effect

According to the first embodiment, even if $CO_2$ is contaminated in the CDA, when abnormal $CO_2$ concentration is detected in the gas in the laser optical path, an alarm can be made by the alarm device 210. Therefore, it is possible to prevent laser operation in a state having a problem of heat lens effect.

The alarm device 210 connected with a $CO_2$ densitometer may also function as a $CO_2$ concentration monitor device for a laser light path in a laser system using a $CO_2$ laser amplifier. According to the first embodiment, beam variation due to a heat lens effect can be suppressed.

6. Second Embodiment

6.1 Configuration

Figure 4:
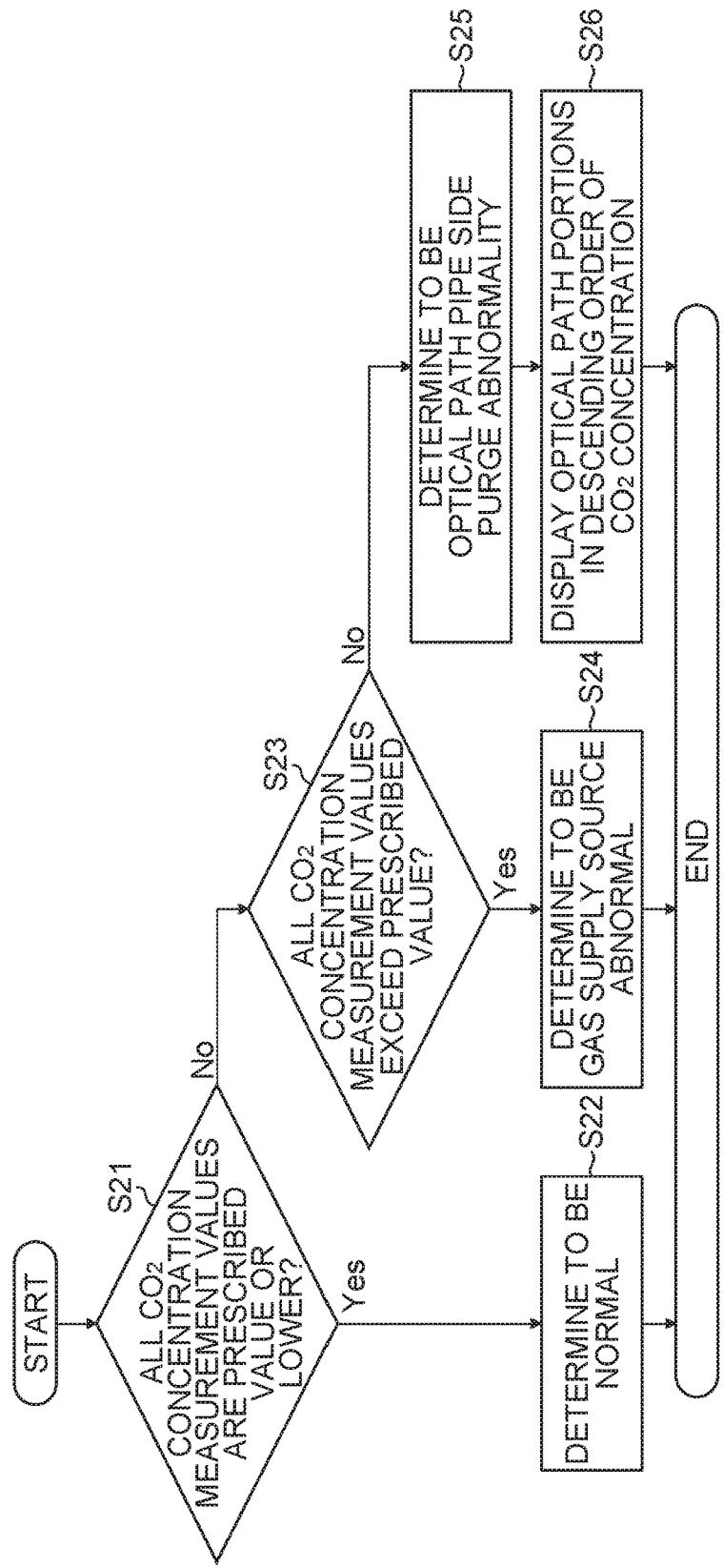
FIG. 4 is a flowchart illustrating an operation of a laser apparatus according to a second embodiment.

FIG. 4 is a flowchart illustrating an operation of a laser apparatus 12 according to a second embodiment. FIG. 4 illustrates a $CO_2$ concentration abnormality determination flow in a laser optical path. The alarm device 210 stores a program of the $CO_2$ concentration abnormality determination flow illustrated in FIG. 4, and executes the flow according to the program.

6.2 Operation

The alarm device 210 can execute the $CO_2$ concentration abnormality determination flow illustrated in FIG. 4 at appropriate timing. For example, before starting laser oscillation by the laser apparatus 12, the alarm device 210 may execute the flow of FIG. 4. The alarm device 210 may execute the flow of FIG. 4 all the time during laser output by the laser apparatus 12.

At step S21, the alarm device 210 determines whether or not all of the $CO_2$ concentration values, measured by the $CO_2$ densitometers 200-205 provided to the laser optical path, are equal to a prescribed value or lower. The "prescribed value" used in the determination process of step S21 means a preset $CO_2$ concentration prescribed value. When different prescribed values are set according to the layout positions of the $CO_2$ densitometers 200-205, the "prescribed value" used in the determination process of step S21 indicates a prescribed value set for each of the $CO_2$ densitometers 200-205. The $CO_2$ concentration abnormality determination processing unit 212 compares $CO_2$ concentration measurement values obtained from the $CO_2$ densitometer 200-205 with the preset $CO_2$ concentration prescribed value.

At step S21, when the $CO_2$ concentration measurement values obtained from all of the $CO_2$ densitometers 200-205 are equal to the prescribed value or lower, the $CO_2$ concentration abnormality determination processing unit 212 moves to step S22.

At step S22, the $CO_2$ concentration abnormality determination processing unit 212 determines that the $CO_2$ concentration in the laser optical path is normal. When the $CO_2$ concentration abnormality determination processing unit 212 determines that it is normal at step S22, the alarm device 210 may display information indicating that the $CO_2$ concentration is normal on the display unit 214, or may not display particular information indicating that it is normal.

At step S21, when the $CO_2$ concentration measurement value obtained from at least one of the $CO_2$ densitometers 200-205 exceeds the prescribed value, the $CO_2$ concentration abnormality determination processing unit 212 moves to step S23.

At step S23, the $CO_2$ concentration abnormality determination processing unit 212 determines whether or not the $CO_2$ concentration measurement values obtained from all of the $CO_2$ densitometers 200-205, provided at various locations on the laser optical path, exceed the prescribed value. When the $CO_2$ concentration in all of the optical path pipes in which the $CO_2$ densitometers 200-205 are provided exceeds the prescribed value, the $CO_2$ concentration abnormality determination processing unit 212 moves to step S24.

At step S24, the $CO_2$ concentration abnormality determination processing unit 212 determines that abnormality occurs in the gas supply source. When the $CO_2$ concentration abnormality determination processing unit 212 determines that abnormality occurs in the gas supply source at step S24, the alarm device 210 displays, on the display unit 214, an alarm indicating that the $CO_2$ concentration in the laser optical path is abnormal. The alarm device 210 may also display, on the display unit 214, information informing that there is a possibility of abnormality in the gas supply source, that is, a failure of the gas supply device 150, for example.

At step S23, when the $CO_2$ concentration measurement values obtained from some of the $CO_2$ densitometers, among the $CO_2$ densitometers 200-205, exceed the prescribed value, the $CO_2$ concentration abnormality determination processing unit 212 moves to step S25.

At step S25, the $CO_2$ concentration abnormality determination processing unit 212 determines that there is purge abnormality on the optical path pipe side. Upon determination that there is purge abnormality on the optical path pipe side at step S25, the $CO_2$ concentration abnormality determination processing unit 212 moves to step S26.

At step S26, the alarm device 210 displays optical path portions in descending order of $CO_2$ concentration, among the optical path portions in which $CO_2$ concentration is measured in the laser optical path. The display of the optical path portions having the $CO_2$ concentration abnormality, at step S26, is an example of an alarm based on the layout positions of the $CO_2$ densitometers. The display of step S26 corresponds to a form of an alarm including "information specifying a position of a laser optical path in which carbon dioxide concentration exceeding a prescribed value is measured".

As for the display contents on the display screen informing optical path portions having $CO_2$ concentration abnormality, various forms are available. Besides the display form described in step S26, it is also possible to display a schematic diagram of laser optical path on the display unit 214 and emphasize or distinguish portions showing abnormal $CO_2$ concentration values on the display screen of the schematic diagram of the optical path. It is only necessary to have a display form in which a location having the $CO_2$ concentration abnormality can be specified in the laser optical path, when the $CO_2$ concentration abnormality is detected by the alarm device 210.

6.3 Effect

According to the second embodiment, it is possible to perform a failure diagnosis of a purge state. Thereby, it is possible to easily specify a location having abnormal $CO_2$ concentration in the laser optical path. Further, according to the second embodiment, it is possible to determine whether the cause of the $CO_2$ concentration abnormality lies on the laser apparatus 12 side or the gas supply device 150 side. As described above, in the second embodiment, an abnormal part and the cause thereof can be found, so that an appropriate action can be taken when abnormality occurs.

7. Third Embodiment

7.1 Configuration

Figure 5:
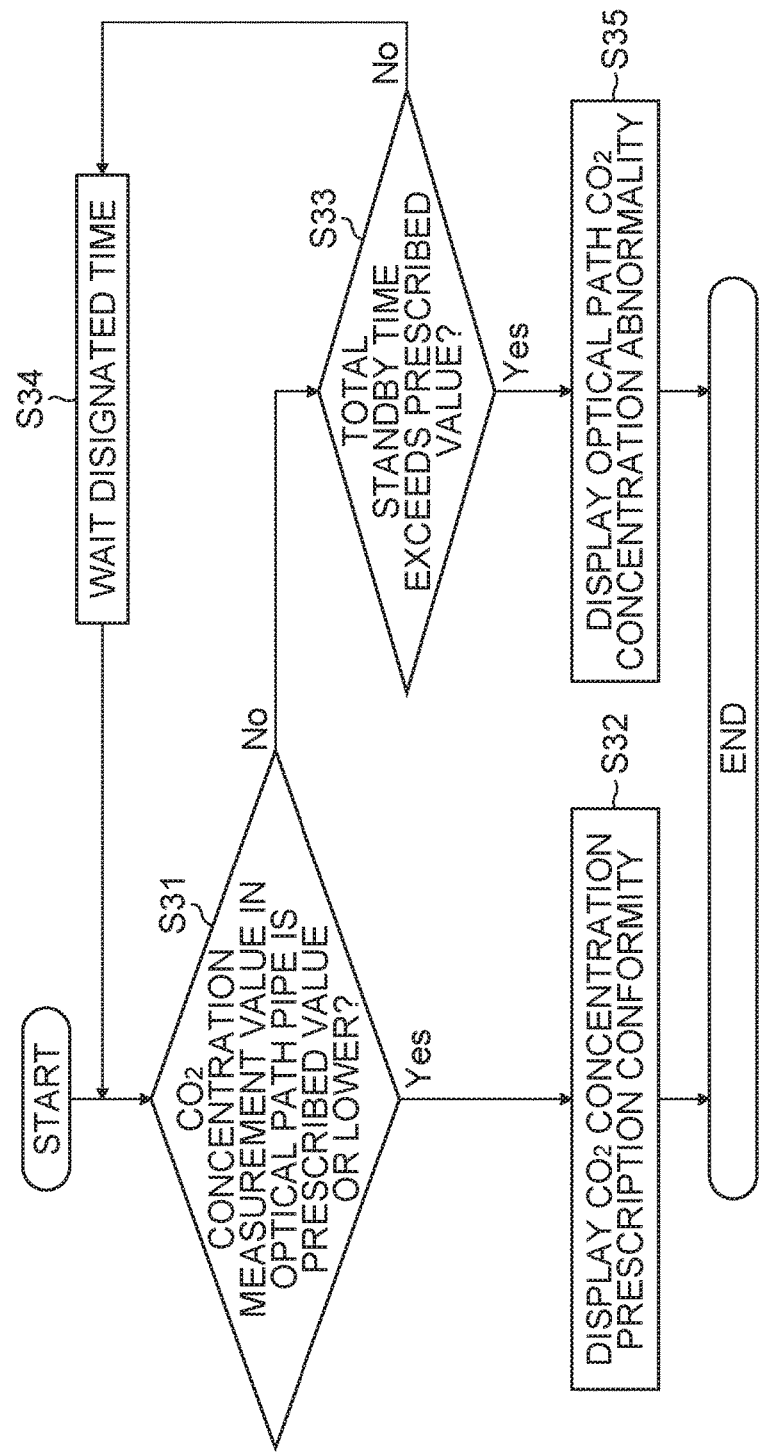
FIG. 5 is a flowchart illustrating an operation of a laser apparatus according to a third embodiment.

FIG. 5 is a flowchart illustrating an operation of a laser apparatus 12 according to a third embodiment. FIG. 5 illustrates a $CO_2$ concentration check flow in the laser optical path, executed at the time of starting laser activation. The check flow illustrated in FIG. 5 is referred to as a "laser activation time $CO_2$ concentration check flow". The alarm device 210 stores a program of the laser activation time $CO_2$ concentration check flow illustrated in FIG. 5, and executes the flow according to the program.

7.2 Operation

Before output of laser light is started by the laser apparatus 12, the alarm device 210 executes the laser activation time $CO_2$ concentration check flow. Operation of the laser apparatus 12 will be described according to the flowchart of FIG. 5.

At step S31, the alarm device 210 determines whether or not the $CO_2$ concentration in the optical path pipe takes a prescribed value or lower. The "prescribed value" used in the determination process of step S31 means a preset $CO_2$ concentration prescribed value. The $CO_2$ concentration abnormality determination processing unit 212 compares $CO_2$ concentration measurement values obtained from the $CO_2$ densitometers 200-205 with the preset $CO_2$ concentration prescribed value. At step S31, upon determining that the $CO_2$ concentration in the optical path pipe takes the prescribed value or lower, the $CO_2$ concentration abnormality determination processing unit 212 moves to step S32.

At step S32, the alarm device 210 performs $CO_2$ concentration prescription conformity indication. The $CO_2$ concentration prescription conformity indication means displaying, on the display unit 214, information indicating that the $CO_2$ concentration in the laser optical path is appropriate concentration having a preset prescribed value or lower. At step S32, the alarm device 210 also determines that laser oscillation is allowed. A signal allowing laser oscillation is transmitted from the alarm device 210 to the laser control unit 50, whereby output of laser light from the laser apparatus 12 is enabled.

At step S31, when the $CO_2$ concentration in the optical path pipe exceeds the prescribed value, the alarm device 210 moves to step S33.

At step S33, the alarm device 210 determines whether or not the total standby time exceeds a prescribed value. Counting of the standby time is started when a signal of a laser activation command is input, for example. The alarm device 210 has a timer not illustrated, and counts the time from activation of the laser apparatus 12 and issues an alarm based on the counted time. Specifically, the alarm device 210 is able to count the total standby time by the timer. The "prescribed value" in step S33 is a time previously designated as an upper limit of the standby time. The prescribed value setting the upper limit of the standby time can be set to an appropriate period of time. For example, it is set to 10 minutes.

At step S33, upon determining that the total standby time does not exceed the prescribed value, the alarm device 210 moves to step S34 and waits a designated time, and then returns to step S31. The designated time of step S34 is a period of time designated as a time interval for measuring the $CO_2$ concentration in the optical path pipe. The designated time may be programmed in advance, or may be set to an appropriate time arbitrarily from a user interface.

When the $CO_2$ concentration in the optical path pipe becomes the prescribed value or lower during standby, the alarm device 210 determines to be Yes at step S31, and moves to step S32 to determine that laser oscillation is allowed.

Meanwhile, at step S33, when the total standby time exceeds the prescribed value of the upper limit, the alarm device 210 moves to step S35. At step S35, the alarm device 210 performs optical path $CO_2$ concentration abnormality indication. The optical path $CO_2$ concentration abnormality indication means displaying information indicating that the $CO_2$ concentration in the laser optical path is abnormal concentration exceeding the preset prescribed value of $CO_2$ concentration. The optical path $CO_2$ concentration abnormality indication corresponds to a form of an "alarm".

At step S35, the alarm device 210 also determines that laser oscillation is not allowed. In that case, a signal not allowing laser oscillation is transmitted from the alarm device 210 to the laser control unit 50. Alternatively, a signal allowing laser oscillation is not transmitted from the alarm device 210 to the laser control unit 50.

7.3 Effect

Conventionally, once a laser optical path is opened to the air at the maintenance time or the like, there is no means for detecting whether CDA purge is performed appropriately in the optical path. According to the third embodiment, it is possible to detect that $CO_2$ concentration in the laser optical path takes an appropriate value equal to or lower than a prescribed value. Further, according to the third embodiment, it is possible to monitor forgetting of attaching an optical path pipe or a laser cover after the maintenance.

8. Fourth Embodiment 8.1 Configuration

Figure 6:
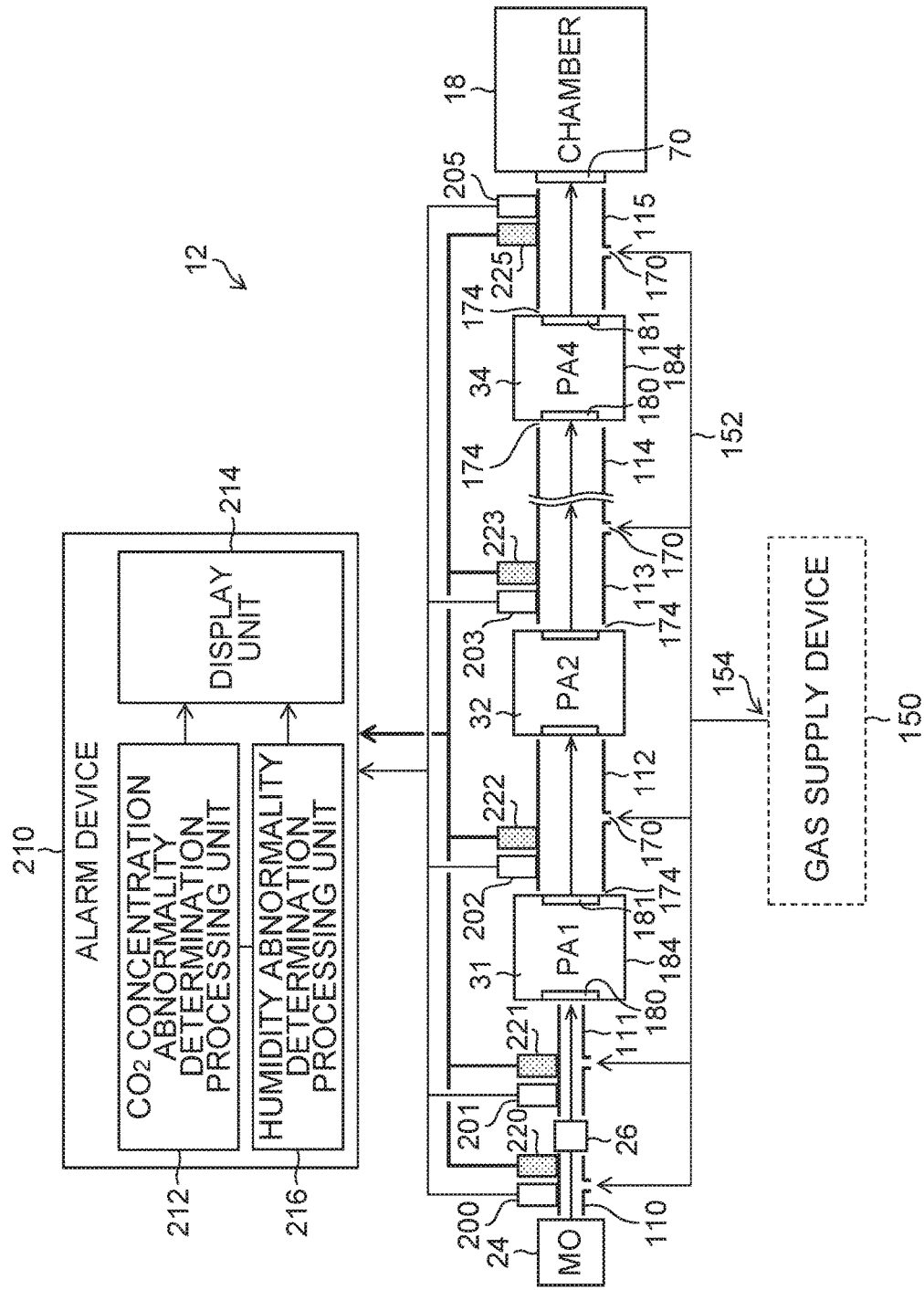
FIG. 6 is a schematic diagram illustrating a configuration of a laser apparatus according to a fourth embodiment.

FIG. 6 is a schematic diagram illustrating a configuration of a laser apparatus according to a fourth embodiment. Different points from FIG. 3 will be described with use of FIG. 6. As illustrated in FIG. 6, a laser apparatus 12 according to the fourth embodiment is configured such that $CO_2$ densitometers 200-205 and hygrometers 220-225 are provided to the respective optical path pipes 110-115 covering the laser optical path. The expression of hygrometers 220-225 means "hygrometers 220, 221, 222, 223, 225 and a hygrometer, not illustrated, provided to the optical path pipe 114". In FIG. 6, the hygrometer provided to the optical path pipe 114 is not illustrated. The hygrometer provided to the optical path pipe 114 may be denoted by a reference numeral 224 in some cases.

The layout positions of the hygrometers 220-225 may be the same as those of the $CO_2$ densitometers 200-205. As for the hygrometers 220-225, hygrometers of an electrostatic capacitance sensor type may be used, for example.

The alarm device 210 includes a humidity abnormality determination processing unit 216. The humidity abnormality determination processing unit 216 performs processing to determine presence or absence of abnormality in humidity, based on humidity measurement results obtained from the hygrometers 220-225.

The display unit 214 displays information informing abnormality in the $CO_2$ concentration and/or the humidity in the laser optical path, based on a determination result of the $CO_2$ concentration abnormality determination processing unit 212 and a determination result of the humidity abnormality determination processing unit 216.

8.2 Operation

To the alarm device 210, a humidity prescribed value is input in addition to a $CO_2$ concentration prescribed value, and information of the $CO_2$ concentration prescribed value and the humidity prescribed value is stored in the alarm device 210. The humidity prescribed value is a value of humidity prescribing the allowable upper limit of humidity in the laser optical path, for example. The humidity prescribed value is used as a determination basis in the case of determining whether the humidity in the laser optical path is normal or abnormal. The humidity prescribed value corresponds to a threshold of the humidity. The humidity prescribed value corresponds to a form of a "prescribed value of humidity". The humidity prescribed value may be set in advance in the alarm device 210, or input from a user interface not illustrated.

As the humidity prescribed value, a uniform value may be set to all of the hygrometers 220-225 provided to the laser optical path. For example, all of the hygrometers 220-225 may be uniformly set to have humidity of 10%. It should be noted that "humidity of 10%" illustrated as an example in the present disclosure is a numerical value expressed as relative humidity at the temperature of 25° C.

Alternatively, the humidity prescribed value may be set according to at least one of the power density of the laser light at the position of an optical path pipe, and a laser light propagation distance in the optical path pipe. Different values may be set to the respective hygrometers 220-225.

For example, the humidity prescribed value of a hygrometer disposed on an optical path pipe of an optical path having low power density may be higher than humidity of 10%. Further, the humidity prescribed value of a hygrometer disposed on an optical path pipe of an optical path having a short laser light propagation distance may be higher than humidity of 10%.

Further, the humidity prescribed value of a hygrometer disposed on the upstream side of the laser optical path may be set higher than the humidity prescribed value of a hygrometer disposed on the downstream side thereof. This means that different humidity prescribed values may be set to at least two hygrometers disposed at different positions, among a plurality of hygrometers.

The alarm device 210 performs comparison with the respective prescribed values for $CO_2$ concentration and humidity, and determines whether both satisfy a laser operation condition. Other operations are similar to the embodiments described above.

8.3 Effect

According to the fourth embodiment, it is possible to monitor both carbon dioxide and moisture that are $CO_2$ laser absorption substances generally existing in the atmosphere. Accordingly, even if the gas supply device 150 is failed and the humidity rises, for example, it is possible to detect the abnormality and avoid laser operation.

9. Fifth Embodiment

9.1 Configuration

Figure 7:
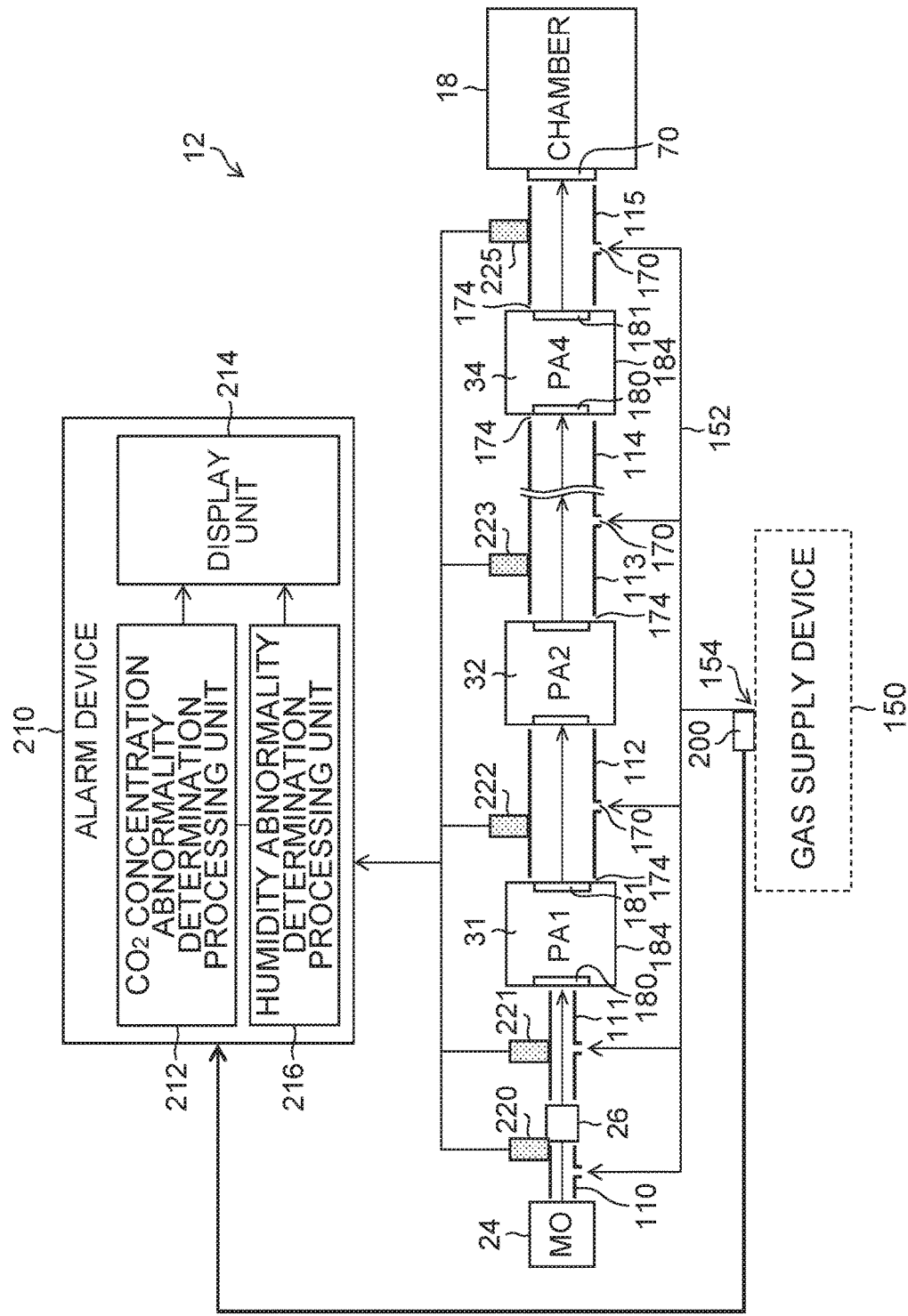
FIG. 7 is a schematic diagram illustrating a configuration of a laser apparatus according to a fifth embodiment.

FIG. 7 is a schematic diagram illustrating part of a configuration of a laser apparatus according to a fifth embodiment. Different points from FIG. 6 will be described with use of FIG. 7. As illustrated in FIG. 7, in the laser apparatus 12 according to the fifth embodiment, the $CO_2$ densitometer 200 is disposed on the pipe 152 connected with the gas supply device 150. It is preferable that the $CO_2$ densitometer 200 is disposed in a pipe portion before the gas supply path is branched to respective optical path pipes by a manifold in the pipe 152. For example, the $CO_2$ densitometer 200 is disposed near the gas supply source of the pipe 152. In FIG. 7, the $CO_2$ densitometer 200 is disposed at the gas introduction part 154 of the pipe 152. The gas introduction part 154 is located near the gas outlet of the gas supply device 150, which may be referred to as a "gas supply device outlet" or a "gas supply source". The $CO_2$ densitometer 200 measures the $CO_2$ concentration in the pipe 152.

As the gas supply device 150, a CDA supply device is used. The CDA supply device may be a facility equipped in a plant where the EUV light generation system 10 is installed.

Compared with the fourth embodiment described in FIG. 6, in the fifth embodiment illustrated in FIG. 7, the optical path pipes 110-115 do not have any $CO_2$ densitometer, and only the hygrometers 220-225 are provided.

A hygrometer may be provided to each of the entire optical path pipes 110-115, or may be provided to some optical path pipes. Alternatively, a hygrometer may be provided to an optical path pipe in which laser light having given power density or higher propagates, among the optical path pipes 110-115. The given power density may be 1.2 $kW/cm^2$, for example. It is preferable that a plurality of hygrometers are disposed in the laser apparatus 12. It is also possible to dispose a plurality of hygrometers on one optical path pipe.

In the laser apparatus 12 in which amplification is performed in stages by the amplifiers 31-34, it is preferable to have a configuration in which a hygrometer is disposed on an optical path pipe covering a laser optical path between amplifiers on the amplification latter-stage side including at least the final-stage amplifier 34. In the case of this example, it is preferable to provide hygrometers in at least the optical path pipes 114 and 115.

In a laser apparatus in which N pieces of $CO_2$ laser amplifiers are used to perform amplification in N stages, it is preferable to have a configuration in which a hygrometer is disposed on an optical path pipe covering a laser optical path between amplifiers on the amplification latter-stage side including at least a final-stage amplifier, among the laser optical paths between the N pieces of amplifies. For example, in the case of using eight amplifiers, it is possible to provide a hygrometer to an optical path pipe covering a laser optical path between amplifiers of the fourth stage and after, respectively.

9.2 Operation

The $CO_2$ concentration abnormality determination processing unit 212 and the humidity abnormality determination processing unit 216 of the alarm device 210 cooperate with each other to determine presence or absence of abnormality in the humidity and the $CO_2$ concentration.

In the gas supply device 150, carbon dioxide is also removed in the process of removing moisture in the process of generating CDA in the device. When abnormality occurs in the process of removing moisture, carbon dioxide concentration in the CDA supplied by the gas supply device 150 may increase. By measuring $CO_2$ concentration by the $CO_2$ densitometer 200 at the outlet of the gas supply device, it is possible to monitor whether the gas supply device 150 operates normally.

Each of the hygrometers 220-225 provided to each of the optical path pipes 110-115 measures humidity in each of the optical path pipes 110-115. When the CDA is supplied from the gas supply device 150 to each optical path pipe, the humidity in the optical path pipe at the normal case takes a value almost similar to that of the CDA management humidity of the gas supply device 150. Accordingly, when it is confirmed that the humidity in the optical path pipe is lowered from the value measured by the hygrometer 220 to the prescribed value or lower, it is estimated that $CO_2$ concentration in the optical path pipe is also lowered to the prescribed $CO_2$ concentration or lower.

On the other hand, when there is abnormality in the laser optical path due to some reasons such as a mounting failure of an optical path pipe, moisture and carbon dioxide in the atmosphere enter the optical path pipe. Humidity and carbon dioxide concentration in the laser optical path have a correlation. When the humidity rises, the carbon dioxide concentration also rises. Accordingly, when it is confirmed that the humidity in the optical path pipe exceeds the prescribed value from the value measured by the hygrometer 220-225, it is estimated that $CO_2$ concentration in the optical path pipe also exceeds the prescribed $CO_2$ concentration. Measuring the humidity in the laser optical path by the hygrometer 220 corresponds to indirectly obtaining information of the $CO_2$ concentration in the laser optical path.

When the alarm device 210 determines, from the value measured by the $CO_2$ densitometer 200, that the $CO_2$ concentration at the outlet of the gas supply device exceeds the prescribed value, the alarm device 210 is able to determine that there is abnormality in the gas supply device 150. In that case, the alarm device 210 issues an alarm informing abnormality in the gas supply source.

When the alarm device 210 determines that the value measured by the $CO_2$ densitometer 200 is prescribed $CO_2$ concentration or lower and that the value measured by any of the hygrometers 220-225 exceeds the prescribed humidity, the alarm device 210 can determine that there is abnormality on the laser optical path side. In that case, the alarm device 210 issues an alarm informing humidity abnormality in the laser optical path.

Each of the hygrometer 222 that measures the humidity in the optical path pipe 112, the hygrometer 223 that measures the humidity in the optical path pipe 113, and a hygrometer, not illustrated, that measures the humidity in the optical path pipe 114, covering the optical path between the amplifiers 31-34, corresponds to a form of a "first hygrometer". Each of the hygrometer 220 that measures the humidity in the optical path pipe 110 and the hygrometer 221 that measures the humidity in the optical path pipe 111 corresponds to a form of a "second hygrometer".

The hygrometer 225 that measures the humidity in the optical path pipe 115 disposed between the amplifier 34 and the chamber 18 corresponds to a form of a "third hygrometer".

9.3 Effect

According to the fifth embodiment, it is possible to monitor both $CO_2$ concentration and humidity by only providing one type of sensor such as a hygrometer, for each of the optical path pipes 110-115.

A hygrometer is less expensive compared with a $CO_2$ densitometer. The laser apparatus 12 applied to the EUV light generation system 10 has a multi-stage amplification system in which a large number of optical path pipes and laser covers are provided. Accordingly, by providing less expensive hygrometers to optical path pipes and laser covers, and disposing the $CO_2$ densitometer 200 at the outlet of the gas supply device, it is possible to reduce the number of $CO_2$ densitometers that are relatively expensive. Thereby, the cost of the entire system can be reduced.

Further, according to the fifth embodiment, as a CDA supply device is used as the gas supply device 150, it is not necessary to supply a special gas such as nitrogen.

The alarm device 210 connected with a hygrometer may also function as a device for monitoring humidity and $CO_2$ concentration in a laser optical path in a laser system using a $CO_2$ laser amplifier.

10. Sixth Embodiment 10.1 Configuration

Figure 8:
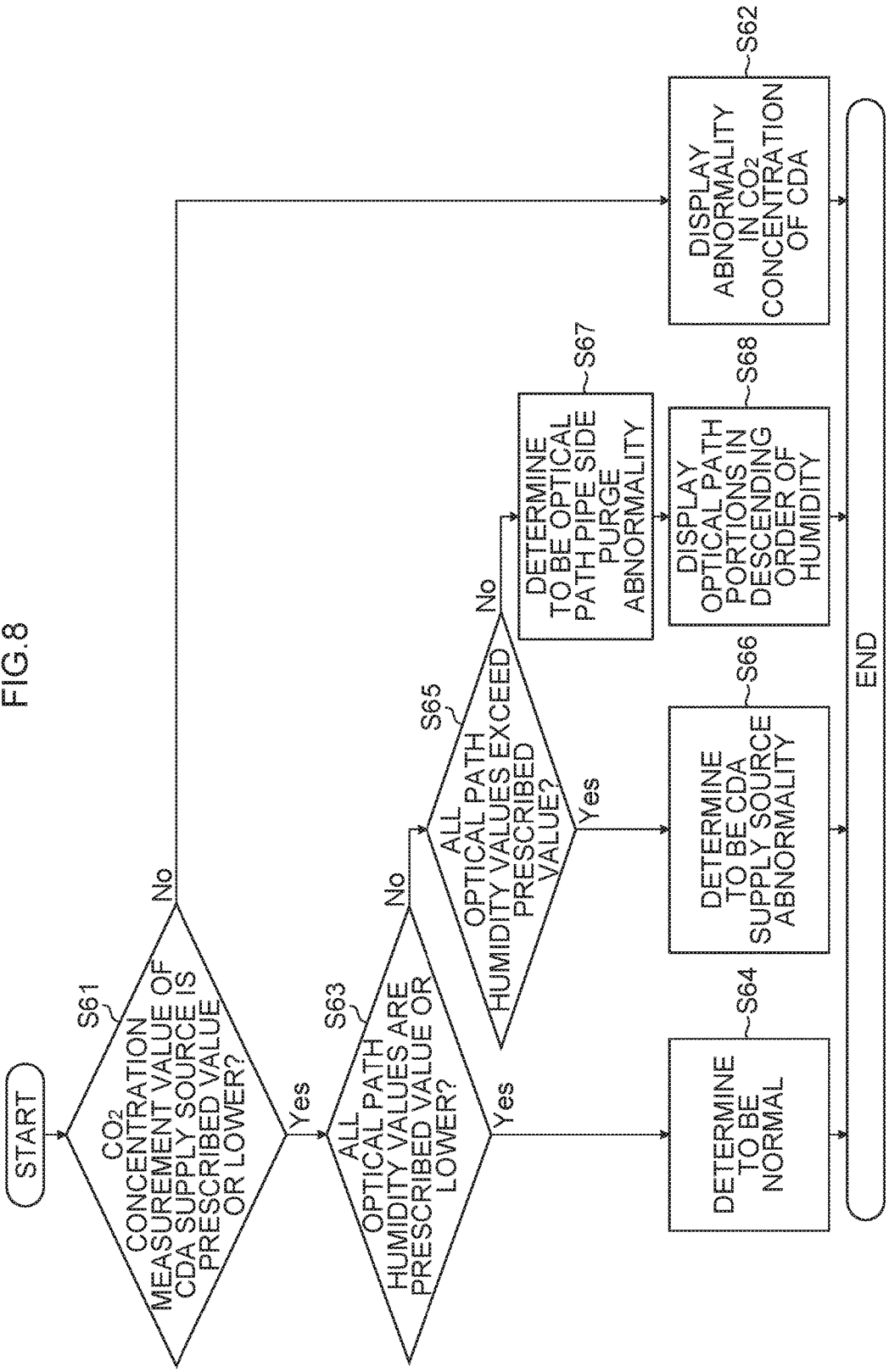
FIG. 8 is a flowchart illustrating an operation of a laser apparatus according to a sixth embodiment.

FIG. 8 is a flowchart illustrating an operation of a laser apparatus 12 according to a sixth embodiment. FIG. 8 illustrates a humidity and $CO_2$ concentration abnormality determination flow. As a device configuration of the sixth embodiment, the configuration described in FIG. 7 is adoptable. The alarm device 210 of the sixth embodiment stores a program of the humidity and $CO_2$ concentration abnormality determination flow illustrated in FIG. 8, and executes the flow according to the program.

10.2 Operation

The alarm device 210 can execute the humidity and $CO_2$ concentration abnormality determination flow illustrated in FIG. 8 at appropriate timing. For example, before starting laser oscillation by the laser apparatus 12, the alarm device 210 may execute the flow of FIG. 8. The alarm device 210 may execute the flow of FIG. 8 all the time during laser output by the laser apparatus 12.

At step S61, the $CO_2$ concentration abnormality determination processing unit 212 determines whether or not the $CO_2$ concentration of the CDA supply source is a prescribed value or lower. $CO_2$ concentration of the CDA supply source has the same meaning as the $CO_2$ concentration at the outlet of the CDA supply device. The "prescribed value" used in the determination process of step S61 means a preset $CO_2$ concentration prescribed value.

At step S61, when the $CO_2$ concentration of the CDA supply source exceeds the prescribed value, the $CO_2$ concentration abnormality determination processing unit 212 determines that there is $CO_2$ concentration abnormality of CDA, and moves to step S62.

At step S62, the alarm device 210 displays that $CO_2$ concentration of CDA is abnormal. The display of $CO_2$ concentration abnormality of CDA at step S62 corresponds to a form of an "alarm".

At step S61, when the $CO_2$ concentration of the CDA supply source is a prescribed value or lower, the $CO_2$ concentration abnormality determination processing unit 212 moves to step S63.

At step S63, the humidity abnormality determination processing unit 216 determines whether or not all optical path humidity values at respective positions in the laser optical path where the hygrometers 220-225 are disposed are the prescribed value or lower. The "prescribed value" used in the determination process of step S63 means a preset humidity prescribed value. When different prescribed values are set according to the layout positions of the hygrometers 220-225, the "prescribed value" used in the determination process of step S63 indicates a prescribed value set for each of the hygrometers 220-225. The humidity abnormality determination processing unit 216 compares the respective humidity measurement values obtained from the hygrometers 220-225 disposed at respective locations on the laser optical path with the preset humidity prescribed value, and determines whether or not all of the humidity measurement values of the hygrometers 220-225 are the prescribed value or lower. The "optical path humidity" is humidity in a laser optical path section of the optical path pipe where the hygrometer 220 is disposed, which means humidity in each optical path pipe.

When all optical path humidity is the prescribed value or lower, the humidity abnormality determination processing unit 216 moves to step S64.

At step S64, the humidity abnormality determination processing unit 216 determines that the humidity and the $CO_2$ concentration in the laser optical path are normal. When the humidity abnormality determination processing unit 216 determines that it is normal at step S64, the alarm device 210 may display, on the display unit 214, information indicating that the humidity and the $CO_2$ concentration are normal, or may not display particular information indicating that they are normal.

At step S63, when at least one of the optical path humidity values measured by the hygrometers 220-225 exceeds the prescribed value, the humidity abnormality determination processing unit 216 moves to step S65.

At step S65, the humidity abnormality determination processing unit 216 determines whether or not all optical path humidity exceeds the prescribed value. The "prescribed value" used in the determination process of step S65 is the same as the "prescribed value" used in the determination process of step S63. When the humidity in all optical path pipes to which the hygrometers 220-225 are provided exceeds the prescribed value, the humidity abnormality determination processing unit 216 moves to step S66.

At step S66, the humidity abnormality determination processing unit 216 determines that abnormality occurs in the CDA supply source. When the humidity abnormality determination processing unit 216 determines that abnormality occurs in the CDA supply source at step S66, the alarm device 210 displays, on the display unit 214, an alarm indicating that the humidity in the laser optical path is abnormal. The alarm device 210 may also display, on the display unit 214, information informing that there is a possibility of abnormality in the CDA supply source, that is, a possibility of a failure of the gas supply device 150, for example.

At step S65, when the humidity measurement values obtained from some of the hygrometers, among the hygrometers 220-225, exceed the prescribed value, the humidity abnormality determination processing unit 216 moves to step S67.

At step S67, the humidity abnormality determination processing unit 216 determines that there is purge abnormality on the optical path pipe side. The humidity abnormality determination processing unit 216 determines that purge abnormality occurs at a location where the humidity is higher than the prescribed value.

Upon determination that there is purge abnormality on the optical path pipe side at step S67, the humidity abnormality determination processing unit 216 moves to step S68.

At step S68, the alarm device 210 displays optical path portions in descending order of humidity, among the optical path portions in which humidity is measured in the laser optical path. The display of the optical path portions with the humidity abnormality at step S68 is an example of an alarm based on the layout positions of the hygrometers. The display of step S68 corresponds to a form of an alarm including "information specifying a position of a laser optical path in which humidity exceeding a prescribed value is measured".

As for the display contents on the display screen informing optical path portions having humidity abnormality, various forms are available. Besides the display form described in step S68, it is also possible to display a schematic diagram of laser optical paths on the display unit 214 and emphasize or distinguish portions where the humidity indicates an abnormal value on the display screen of the schematic diagram of the optical paths. It is only necessary to have a display form in which a location of humidity abnormality can be specified in the laser optical path, when the humidity abnormality is detected by the alarm device 210.

10.3 Effect

According to the sixth embodiment, it is possible to perform a failure diagnosis in a purge state. Thereby, it is possible to easily specify an abnormal part. Further, according to the sixth embodiment, it is possible to determine whether the cause of abnormality in humidity and/or $CO_2$ concentration lies on the laser apparatus 12 side or the gas supply device 150 side. As described above, in the sixth embodiment, an abnormal part and the cause thereof can be found, so that an appropriate action can be taken when abnormality occurs.

11. Seventh Embodiment

11.1 Configuration

FIG. 9 is a flowchart illustrating an operation of a laser apparatus 12 according to a seventh embodiment. FIG. 9 illustrates a humidity and $CO_2$ concentration check flow, executed at the time of starting laser activation. The check flow illustrated in FIG. 9 is referred to as a "humidity and $CO_2$ concentration check flow at the time of laser activation". As a device configuration of the seventh embodiment, the configuration described in FIG. 7 is adoptable. The alarm device 210 stores a program of the humidity and $CO_2$ concentration check flow at the time of laser activation illustrated in FIG. 9, and executes the flow according to the program.

11.2 Operation

Before output of laser light is started by the laser apparatus 12, the alarm device 210 executes the humidity and $CO_2$ concentration check flow at the time of laser activation. This means that the alarm device 210 executes a flow of checking the $CO_2$ concentration at the outlet of the gas supply device and the humidity in the optical path, at the time of starting laser activation. Operation of the laser apparatus 12 will be described according to the flowchart of FIG. 9.

At step S71, the $CO_2$ concentration abnormality determination processing unit 212 determines whether or not the $CO_2$ concentration of the CDA supply source is a prescribed value or lower. The "prescribed value" used in the determination process of step S71 means a preset $CO_2$ concentration prescribed value. When the $CO_2$ concentration of the CDA supply source exceeds the prescribed value, the $CO_2$ concentration abnormality determination processing unit 212 determines that there is $CO_2$ concentration abnormality of CDA, and moves to step S72.

At step S72, the alarm device 210 displays that $CO_2$ concentration of CDA is abnormal. The display of $CO_2$ concentration abnormality of CDA at step S72 corresponds to a form of an "alarm". When the alarm device 210 displays abnormality in $CO_2$ concentration of CDA at step S72, the alarm device 210 determines that laser oscillation is not allowed. In that case, a signal not allowing laser oscillation is transmitted from the alarm device 210 to the laser control unit 50. Alternatively, a signal allowing laser oscillation is not transmitted from the alarm device 210 to the laser control unit 50. Thereby, the laser control unit 50 stops the process of activating the laser apparatus 12.

At step S71, when the $CO_2$ concentration of the CDA supply source is a prescribed value or lower, the alarm device 210 moves to step S73.

At step S73, the humidity abnormality determination processing unit 216 determines whether or not the humidity in the optical path pipe is a prescribed value or lower. The "prescribed value" used in the determination process of step S73 means a preset humidity prescribed value. Upon determining that the humidity in each of the optical path pipes takes the prescribed value or lower, the humidity abnormality determination processing unit 216 moves to step S74.

At step S74, the alarm device 210 performs humidity prescription conformity indication. The humidity prescription conformity indication means displaying, on the display unit 214, information indicating that the humidity in the laser light path is appropriate humidity having a preset prescribed value or lower. Further, at step S74, the alarm device 210 also determines that laser oscillation is allowed. A signal allowing laser oscillation is transmitted from the alarm device 210 to the laser control unit 50, whereby output of laser light from the laser apparatus 12 is enabled.

At step S73, when the humidity in the optical path pipe exceeds the prescribed value, the humidity abnormality determination processing unit 216 moves to step S75.

At step S75, the humidity abnormality determination processing unit 216 determines whether or not the total standby time exceeds a prescribed value. The "prescribed value" used in the determination process of step S75 is a time previously designated as an upper limit of the standby time, which is set to ten minutes, for example.

At step S75, upon determining that the total standby time does not exceed the prescribed value, the humidity abnormality determination processing unit 216 moves to step S76 and waits a designated period of time, and then returns to step S73. When the humidity in the optical path pipe becomes the prescribed value or lower during standby, the alarm device 210 moves to step S74 to determine that laser oscillation is allowed.

Meanwhile, at step S75, when the total standby time exceeds the upper limit prescribed value, the alarm device 210 moves to step S77. At step S77, the alarm device 210 performs humidity abnormality indication. The humidity abnormality indication means displaying information indicating that the humidity in the laser optical path is abnormal humidity exceeding the preset prescribed value. The humidity abnormality indication corresponds to a form of an "alarm".

At step S77, the alarm device 210 also determines that laser oscillation is not allowed. In that case, a signal not allowing laser oscillation is transmitted from the alarm device 210 to the laser control unit 50. Alternatively, a signal allowing laser oscillation is not output from the alarm device 210 to the laser control unit 50. Thereby, the laser control unit 50 stops the process of activating the laser apparatus 12.

11.3 Effect

According to the seventh embodiment, it is possible to detect that each of humidity and $CO_2$ concentration in the laser optical path takes an appropriate value equal to or lower than the prescribed value. Further, according to the seventh embodiment, it is possible to monitor forgetting of attaching an optical path pipe or a laser cover after the maintenance.

The description provided above is intended to provide just examples without any limitations. Accordingly, it will be obvious to those skilled in the art that changes can be made to the embodiments of the present disclosure without departing from the scope of the accompanying claims.

The terms used in the present description and in the entire scope of the accompanying claims should be construed as terms "without limitations". For example, a term "including" or "included" should be construed as "not limited to that described to be included". A term "have" should be construed as "not limited to that described to be held". Moreover, an indefinite article "a/an" described in the present description and in the accompanying claims should be construed to mean "at least one" or "one or more".

What is claimed is:

1. A laser apparatus comprising:
   a master oscillator configured to output laser light;
   a plurality of amplifiers each configured to include carbon dioxide as a laser medium and amplify the laser light;
   a first optical path pipe configured to cover a laser optical path between the amplifiers;
   a gas supply port configured to supply gas into the first optical path pipe, the gas having lower carbon dioxide concentration than carbon dioxide concentration of air;
   a first carbon dioxide densitometer configured to measure carbon dioxide concentration in the first optical path pipe; and
   an alarm device to which a measurement result of the first carbon dioxide densitometer is input, the alarm device being configured to issue an alarm when the carbon dioxide concentration measured by the first carbon dioxide densitometer exceeds a preset prescribed value of carbon dioxide concentration.

2. The laser apparatus according to claim 1, wherein
   a plurality of the first carbon dioxide densitometers are disposed, and
   the alarm device issues the alarm based on layout positions of the first carbon dioxide densitometers, and the alarm includes information specifying a position of the laser optical path in which the carbon dioxide concentration exceeding the prescribed value is measured.

3. The laser apparatus according to claim 1, wherein
   the alarm device is configured to count a time from activation of the laser apparatus, and issues the alarm based on a counted time,
   an upper limit of a standby time is set to the alarm device, and
   the alarm is issued when the carbon dioxide concentration measured by the first carbon dioxide densitometer exceeds the prescribed value and the counted time exceeds the upper limit of the standby time.

4. The laser apparatus according to claim 1, further comprising
   a hygrometer configured to measure humidity in the first optical path pipe, wherein
   a measurement result of the hygrometer is input to the alarm device, and the alarm device issues the alarm when the humidity measured by the hygrometer exceeds a preset prescribed value of humidity.

5. The laser apparatus according to claim 1, wherein
   windows are disposed on both sides of the first optical path pipe.

6. The laser apparatus according to claim 1, wherein
   N pieces of the amplifiers are disposed, the N being an integer of 3 or larger, and
   the first carbon dioxide densitometer is disposed on the first optical path pipe covering, among laser optical paths between the N pieces of the amplifiers, a laser optical path between the amplifiers on an amplification latter-stage side including at least the amplifier of a final stage.

7. The laser apparatus according to claim 1, further comprising:
   a second optical path pipe configured to cover the laser optical path between the master oscillator and the amplifier; and
   a second carbon dioxide densitometer configured to measure carbon dioxide concentration in the second optical path pipe, wherein:
   the gas is supplied to the second optical path pipe, and
   a measurement result of the second carbon dioxide densitometer is input to the alarm device, and the alarm device issues an alarm when the carbon dioxide concentration measured by the second carbon dioxide densitometer exceeds a preset prescribed value of carbon dioxide concentration.

8. The laser apparatus according to claim 1, further comprising:
a third optical path pipe configured to cover the laser optical path through which laser light output from an amplifier of a final stage among the amplifiers is transmit; and
a third carbon dioxide densitometer configured to measure carbon dioxide concentration in the third optical path pipe, wherein:
the gas is supplied to the third optical path pipe, and
a measurement result of the third carbon dioxide densitometer is input to the alarm device, and the alarm device issues an alarm when the carbon dioxide concentration measured by the third carbon dioxide densitometer exceeds a preset prescribed value of carbon dioxide concentration.

9. The laser apparatus according to claim 8, wherein:
the prescribed value of the carbon dioxide concentration is set according to at least one of power density of laser light at a position of the optical path pipe at which any carbon dioxide densitometer of the plurality of the carbon dioxide densitometers including the first carbon dioxide densitometer and the third carbon dioxide densitometer is disposed, and a laser light propagation distance of the optical path pipe at which any carbon dioxide densitometer of the plurality of the carbon dioxide densitometers is disposed, and
different values are set to at least two carbon dioxide densitometers disposed at different positions among the plurality of the carbon dioxide densitometers.

10. An extreme ultraviolet light generation system comprising:
the laser apparatus according to claim 8;
a chamber into which laser light output from the laser apparatus is introduced; and
a target feeder configured to feed a target into the chamber, wherein:
the third optical path pipe is connected with the chamber, and
the target supplied from the target feeder into the chamber is irradiated with laser light output from the laser apparatus and made into plasma, and extreme ultraviolet light is generated.

11. A laser apparatus comprising:
a master oscillator configured to output laser light;
a plurality of amplifiers each configured to include carbon dioxide as a laser medium and amplify the laser light;
a first optical path pipe configured to cover a laser optical path between the amplifiers;
a gas supply port configured to supply gas into the first optical path pipe, the gas having lower carbon dioxide concentration than carbon dioxide concentration of air;
a carbon dioxide densitometer configured to measure carbon dioxide concentration of the gas supplied from the gas supply port;
a first hygrometer configured to measure humidity in the first optical path pipe, and
an alarm device to which a measurement result of the carbon dioxide densitometer and a measurement result of the first hygrometer are input, the alarm device being configured to issue an alarm in both cases where the carbon dioxide concentration measured by the carbon dioxide densitometer exceeds a preset prescribed value of carbon dioxide concentration, and where the humidity measured by the first hygrometer exceeds a preset prescribed value of humidity.

12. The laser apparatus according to claim 11, wherein:
a plurality of the first hygrometers are disposed, and
the alarm device issues the alarm based on layout positions of the first hygrometers, and the alarm includes information specifying a position of the laser optical path in which the humidity exceeding the prescribed value of humidity is measured.

13. The laser apparatus according to claim 11, wherein:
the alarm device is configured to count a time from activation of the laser apparatus, and issues the alarm based on a counted time,
an upper limit of a standby time is set to the alarm device, and
the alarm device issues an alarm informing the humidity abnormality when the humidity measured by the first hygrometer exceeds the prescribed value of humidity and the counted time exceeds the upper limit of the standby time.

14. The laser apparatus according to claim 11, further comprising
a pipe configured to supply the gas to the first optical path pipe, wherein:
the gas supply port is a gas introduction part of the pipe, and
the carbon dioxide densitometer is disposed on the pipe.

15. The laser apparatus according to claim 11, wherein:
windows are disposed on both sides of the first optical path pipe.

16. The laser apparatus according to claim 11, wherein:
N pieces of the amplifiers are disposed, the N being an integer of 3 or larger, and
the first hygrometer is disposed on the first optical path pipe covering, among the laser optical paths between the N pieces of the amplifiers, a laser optical path between the amplifiers on an amplification latter-stage side including at least the amplifier of a final stage.

17. The laser apparatus according to claim 11, further comprising:
a second optical path pipe configured to cover the laser optical path between the master oscillator and the amplifier; and
a second hygrometer configured to measure humidity in the second optical path pipe, wherein:
the gas is supplied to the second optical path pipe, and
a measurement result of the second hygrometer is input to the alarm device, and the alarm device issues an alarm when the humidity measured by the second hygrometer exceeds a preset prescribed value of humidity.

18. The laser apparatus according to claim 11, further comprising:
a third optical path pipe configured to cover the laser optical path for transmitting laser light output from an amplifier of a final stage among the plurality of the amplifiers; and
a third hygrometer configured to measure humidity in the third optical path pipe, wherein:
the gas is supplied to the third optical path pipe, and
a measurement result of the third hygrometer is input to the alarm device, and the alarm device issues an alarm when the humidity measured by the third hygrometer exceeds a preset prescribed value of humidity.

19. The laser apparatus according to claim 18, wherein:
the prescribed value of humidity is set according to at least one of power density of laser light at a position of the optical path pipe at which any hygrometer of the plurality of the hygrometers including the first hygrometer and the third hygrometer is disposed, and a laser light propagation distance of the optical path pipe at which any hygrometer of the plurality of the hygrometers is disposed, and different values are set to at least two hygrometers disposed at different positions among the plurality of the hygrometers.

20. An extreme ultraviolet light generation system comprising:

the laser apparatus according to claim 18;

a chamber into which laser light output from the laser apparatus is introduced; and a target feeder configured to feed a target into the chamber, wherein:

the third optical path pipe is connected with the chamber, and the target supplied from the target feeder into the chamber is irradiated with laser light output from the laser apparatus and made into plasma, and extreme ultraviolet light is generated.

* * * * *